US007524487B2

(12) United States Patent
Mosser et al.

(10) Patent No.: US 7,524,487 B2
(45) Date of Patent: Apr. 28, 2009

(54) COMPOSITIONS AND METHODS FOR MODULATING INTERLEUKIN-10

(75) Inventors: David M. Mosser, Hyattsville, MD (US); Mark Lucas, Cambridge (GB)

(73) Assignee: University of Maryland, College Park, MD (US)

( * ) Notice: Subject to any disclaimer, the term of this patent is extended or adjusted under 35 U.S.C. 154(b) by 0 days.

(21) Appl. No.: 11/406,552

(22) Filed: Apr. 19, 2006

(65) Prior Publication Data

US 2006/0251733 A1 Nov. 9, 2006

Related U.S. Application Data

(60) Provisional application No. 60/673,275, filed on Apr. 19, 2005, provisional application No. 60/686,478, filed on Jun. 1, 2005, provisional application No. 60/704,007, filed on Jul. 29, 2005.

(51) Int. Cl.
*A61K 38/19* (2006.01)
*A61K 30/02* (2006.01)
(52) U.S. Cl. .................................. 424/85.1; 424/184.1
(58) Field of Classification Search ........................ None
See application file for complete search history.

(56) References Cited

U.S. PATENT DOCUMENTS

| 6,660,266 | B1 | 12/2003 | Mosser et al. |
| 2003/0091533 | A1 | 5/2003 | Van et al. |
| 2003/0091562 | A1 | 5/2003 | Jakobovits et al. |
| 2003/0105057 | A1 | 6/2003 | Fu et al. |

OTHER PUBLICATIONS

Boehringer et al . (Jun. 1999), Eur. Cytokine Netw., vol. 10, No. 2, pp. 211-217.*
Benkhart, Elke M., et al., "Role of Stat3 in Lipopolysaccharide-Induced IL-10 Gene Expression," *J. Immunology*, 165: 1612-1617 (2000).
Bogdan, Christian, et al., "Macrophage Deactivation by Interleukin 10," *J. Exp. Med.*, 174: 1549-1555 (1991).
Brightbill, Hans D., et al., "A Prominent Role for Sp1 During Lipopolysaccharide-Mediated Induction of the IL-10 Promoter in Macrophages," *J. Immunology*, 164: 1940-1951 (2000).
D'Andrea, Annalisa, et al., "Interleukin 10 (IL-10) Inhibits Human Lymphocyte Interferon γ-Production by Suppressing Natural Killer Cell Stimulatory Factor/IL-12 Synthesis in Accessory Cells," *J. Exp. Med.*, 178: 1041-1048 (1993).
Fiorentino, David F., et al., "IL-10 Acts on the Antigen-Presenting Cell to Inhibit Cytokine Production by Th1 Cells," *J. Immunology*, 146(10): 3444-3451 (1991).
Gerber, Jeffrey S. and Mosser, David M., "Reversing Lipopolysaccharide Toxicity by Ligating the Macrophage Fcγ Receptors," *J. Immunology*, 166: 6861-6868 (2001).
Goriely, Stanislas, et al., "Human *IL-12(p35)* Gene Activation Involves Selective Remodeling of a Single Nucleosome within a Region of the Promoter Containing Critical Sp1-Binding Sites," *Blood*, 101(12): 4894-4902 (2003).
Guo, Xuecui, "Defining the Involvement of p38α MAPK in the Production of Anti- and Proinflammatory Cytokines Using an SB 203580-resistant Form of the Kinase," *J. Biological Chemistry*, 278(25): 22237-22242 (2003).
Hart, P.H., et al., "Comparison of the Suppressive Effects of Interleukin-10 and Interleukin-4 on Synovial Fluid Macrophages and Blood Monocytes from Patients with Inflammatory Arthritis," *Immunology*, 84: 536-542 (1995).
Im, Sin-Hyeog, et al., "Chromatin-level Regulation of the *IL10* Gene in T Cells," *J. Biological Chemistry*, 279(45): 46818-46825 (2004).
Liu, Yi-Wen, et al., "Functional Cooperation of Simian Virus 40 Promoter Factor 1 and CCAAT/Enhancer-Binding Protein β and δ in Lipopolysaccharide-Induced Gene Activation of IL-10 in Mouse Macrophages," *J. Immunology*, 171: 821-828 (2003).
Lucas, Mark, et al., "ERK Activation Following Macrophage FcγR Ligation Leads to Chromatin Modifications at the IL-10 Locus," *J. Immunology*, 175: 469-477 (2005).
Ma, Wei, et al., "The p38 Mitogen-activated Kinase Pathway Regulates the Human Interleukin-10 Promoter via the Activation of Sp1 Transcription Factor in Lipopolysaccharide-stimulated Human Macrophages," *J. Biological Chemistry*, 276(17): 13664-13674 (2001).
Malefyt, René de Waal, et al., "Interleukin 10 (IL-10) and Viral IL-10 Strongly Reduce Antigen-specific Human T Cell Proliferation by Diminishing the Antigen-presenting Capacity of Monocytes via Downregulation of Class II Major Histocompatibility Complex Expression," *J. Exp. Med.*, 174: 915-924 (1991).
Mathur, Ram Kumar, et al., "Reciprocal CD40 Signals Through p38MAPK and ERK-1/2 Induce Counteracting Immune Responses," *Nature Medicine*, 10(5): 540-544 (2004).
Mosser, David M., "The Many Faces of Macrophage Activation," *J. Leukocyte Biology*, 73: 209-212 (2003).
Murphy, Kenneth M. and Reiner, Steven L., "The Lineage Decisions of Helper T Cells," *Nature Reviews, Immunology*, 2: 933-944 (2002).
Sutterwala, Fayyaz S., et al., "Selective Suppression of Interleukin-12 Induction after Macrophage Receptor Ligation," *J. Exp. Med.*, 185(11): 1977-1985 (1997).
Thomson, Stuart, et al., "The Nucleosomal Response Associated with Immediate-Early Gene Induction is Mediated via Alternative MAP Kinase Cascades: MSK1 as a Potential Histone H3/HMG-14 Kinase," *The EMBO Journal*, 18(17): 4779-4793 (1999).

* cited by examiner

*Primary Examiner*—Prema Mertz
(74) *Attorney, Agent, or Firm*—Elmore Patent Law Group, P.C.; Darlene A. Vanstone; Carolyn S. Elmore

(57) ABSTRACT

The present invention provides compositions and methods for upregulating IL-10 production in a stimulated cell. In one aspect, the invention provides methods of identifying ERK activating agents capable of activating and amplifying the ERK MAPK pathway in a cell. Such ERK activating agents are capable of upregulating the production of IL-10 in stimulated cells. In another aspect, the invention provides ERK activating agents identified by the screening methods of the invention. Methods are also provided for preventing and treating inflammation in a susceptible patient by administering to the patient, a therapeutically effective amount of an ERK activating agent identified in accordance with the invention.

8 Claims, 25 Drawing Sheets

A. IP:phospho-H3

IP:acetyl-H3

B.

COMPOSITIONS AND METHODS FOR MODULATING INTERLEUKIN-10

RELATED APPLICATION(S)

This application claims the benefit of U.S. Provisional Application No's. 60/673,275, filed on Apr. 19, 2005, 60/686,478, filed on Jun. 1, 2005, and 60/704,007, filed on Jul. 29, 2005. The entire teachings of the above application(s) are incorporated herein by reference.

GOVERNMENT SUPPORT

The invention was supported, in whole, or in part, by NIH grant number RO1 AI49383-03. The Government has certain rights in the invention.

BACKGROUND OF THE INVENTION

Macrophages are prodigious secretory cells which can produce a number of molecules which can either potentiate or dampen immune responses (Nathan, J. Clin. Invest. 79:319-322, 1987). In response to infectious or inflammatory stimuli, macrophages can produce several proinflammatory molecules, including TNF.alpha., IL-1, IL-6 and IL-12 (Nathan, J. Clin. Invest. 79:319-322, 1987; Trinchieri et al., J. Leukocyte Biol. 59:505-511, 1996). These proinflammatory molecules are important for host defense, because experimentally infected animals deficient in these cytokines are invariably more susceptible to acute bacterial infections than are normal animals (Dalrymple et al., Infect. Immun. 63:2262-2268, 1995; Kincy-Cain et al., Infect. Immun. 64:1437-1440, 1996).

In many instances, macrophages can participate in the regulation of proinflammatory cytokines by the production of anti-inflammatory molecules. The secretion of glucocorticoids, TGF beta, and IL-10 by macrophages has been associated with anti-inflammatory responses (Tsunawaki et al., Nature 334:260-262, 1988; Bogdan et al., J. Exp. Med. 174:1549-1555, 1991; Kunkel et al., J. Biol. Chem. 263:5380-5384, 1988). These anti-inflammatory molecules have the potential to ameliorate the potentially deleterious effects of an overly aggressive immune response. Thus, the balance between the secretion of pro- and anti-inflammatory molecules by macrophages is a critical component of the acute phase response and has the potential to affect the adaptive immune response that subsequently develops.

Interleukin-10 (IL-10) is an 18 kDa cytokine produced by the Th2 subset of CD4+ helper cells. It is also produced by some activated B cells, by some Th1 cells (in humans), by activated macrophages, and by some non-lymphocytic cell types (e.g., keratinocytes). In contrast to IL-12, IL-10 has been associated with an inhibition of Th1-type immune responses. IL-10 has been shown to inhibit the production of Th1 cytokines and the proliferation of Th1 cells to antigen (Malefyt et al., J. Exp. Med. 174:915-924, 1991; Fiorentino et al., J. Immunol. 146:3444-3451, 1991). IL-10 inhibits IL-12 production by macrophages (D'Andrea et al., J. Exp. Med. 178:1041-1048, 1993), and the administration of exogenous IL-10 can diminish the toxicity of LPS (Howard et al., J. Exp. Med. 177:1205-1208, 1993; Berg et al., J. Clin. Invest. 96:2339-2347, 1995). IL-10 has been considered for the treatment of autoimmune diseases such as arthritis (Hart et al., Immunology 84:536-542, 1995) and colitis (Davidson et al., J. Exp. Med. 184:241-251, 1996), and recently for psoriasis Mitogen-activated protein kinases (MAPKs) are members of conserved signal transduction pathways that activate transcription factors, translation factors and other target molecules in response to a variety of extracellular signals. In mammalian cells, three parallel MAPK pathways have been described. One MAPK pathway leads to the activation of the extracellular-signal-regulated kinase (ERK). Other signal transduction pathways leading to the activation of the cJun N-terminal kinase (JNK) and the p38 MAPK (for reviews, see Davis, Trends Biochem. Sci. 19:470-473 (1994); Cano and Mahadevan, Trends Biochem. Sci. 20:117-122(1995)). Previous studies conducted by the inventors (see U.S. Pat. No. 6,660,266) have indicated that ligation of the Fcγ receptor (FcR) on macrophages, in the presence of what would normally be an inflammatory stimulus, inhibits IL-12 release and induces high levels of IL-10 production. The inventors have since learned that FcR ligation may cause amplification the p38 and ERK MAPK pathways, and enhance Toll-like receptor (TLR)-induced IL-10 production, thus increasing the anti-inflammatory response potential of activated macrophages. This observation has lead to the discovery of a novel class of anti-inflammatory compounds that would work by enhancing ERK MAPK levels in cells such as leukocytes.

SUMMARY OF THE INVENTION

The present invention provides compositions and methods for upregulating IL-10 production in a stimulated cell. In one aspect, the invention provides methods of identifying ERK activating agents capable of activating and amplifying the ERK MAPK pathway in a cell. Such ERK activating agents are in turn capable of upregulating the production of IL-10 in stimulated cells. In another aspect, the invention provides ERK activating agents identified by the screening methods of the invention. Methods are also provided for preventing and treating inflammation in a susceptible patient by administering to the patient, a therapeutically effective amount of an ERK activating agent identified in accordance with the invention.

Abbreviations Used:

IC, immune complex; PMA, phorbol 12-myristate 13-acetate; RT-PCR, real time (also known as reverse transcription) polymerase chain reaction; BMMφ, bone marrow derived macrophages; Mφ, macrophage; LPS, lipopolysaccharide; IL-10, interleukin 10; IL, interleukin; mIL-10, murine interleukin 10; TLR, toll-like receptor; QRT-PCR, quantitataive real time polymerase chain reaction; EMSA, electrophoretic mobility shift assay; ELISA, enzyme linked immunosorbent assay; ChIP, chromatin immunoprecipitation; FcR or FcγR, receptor for the Fc portion of immunoglobulin molecule; siRNA, small interferring ribonucleic acid; CSF-1, colony stimulating factor 1.

DETAILED DESCRIPTION OF THE INVENTION

Figure 1:
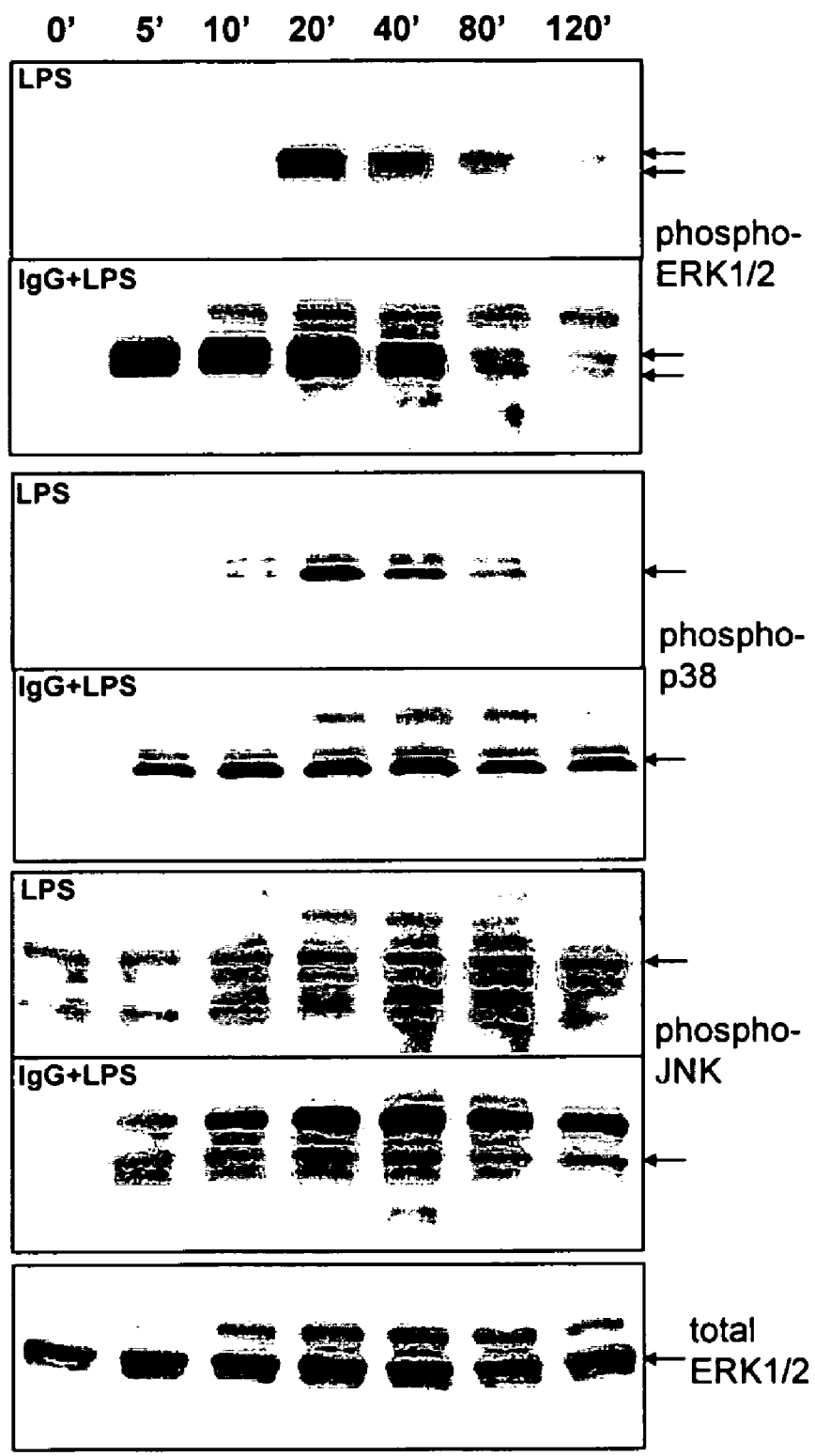
FIG. 1 is a Western blot showing the kinetics of MAPK activation in bone marrow derived macrophages (BMMφ) stimulated with (LPS) alone or LPS in combination with E-IgG, an immune complex that ligates the FcγR. BMMφ were stimulated with LPS (10 ng/ml)±E-IgG. Cells were then lysed at the indicated times and equal amounts of whole cell lysates were separated by SDS PAGE and analyzed by Western blotting using phospho-specific Abs to ERK1/2, p38 or JNK. Total ERK1/2 (bottom panel) was used as the loading control.

Macrophage activation by TLR agonists results in the production of proinflammatory cytokines, such as IL-12 and low levels of anti-inflammatory cytokine IL-10. Previously, the inventors have shown that ligation of the FcR on macrophages in the presence of what would normally be an inflammatory stimulus, inhibits IL-12 release and induces high levels of IL-10 production (see U.S. Pat. No. 6,660,266). The inventors have now discovered that increased IL-10 production results from the rapid and enhanced activation of both the p38 and ERK MAPK cascades.

Blockade of either the ERK or p38, but not the JNK, MAPK pathway by pharmacological inhibitors or by siRNA resulted in significant inhibition of IL-10. Further evidence that ERK was necessary for augmented IL-10 was shown by temporal separation of FcR and TLR activation after loss of ERK, but not p38, phosphorylation, which resulted in diminished IL-10. The activation of ERK and p38 MAPK pathways by FcR alone does not induce IL-10, but requires nuclear factor-kB (NF-kB) and/or p38 activation by TLR ligation. NF-kB is an essential transcription factor that is ubiquitous to most cell types and whose activity is modulated by a wide range of inducers including cytokines and bacterial or viral products. Thus, the inventors believe that FcR-ligation amplifies ERK MAPK pathways, thereby enhancing TLR-induced IL-10 production, and therefore providing a mechanism of increasing the anti-inflammatory potential of activated macrophages.

In accordance with the invention, methods are provided for upregulating IL-10 production in a stimulated cell comprising contacting the cell with an ERK activating agent identified in accordance with the invention.

In one embodiment, methods of upregulating IL-10 production above that in resting cells in a macrophage-like cell in response to an inflammatory stimulus comprising contacting said cell with a composition comprising an ERK activating agent in combination with a phosphatase inhibitor are provided.

The phosphatase inhibitors used to practice the present invention may be any that is known, or discovered to inhibit the phosphatase enzyme, and are not limited to any particular structural class of compounds. As used herein, the term "phosphatase inhibitors" includes any pharmaceutically acceptable salts thereof. The assay for identifying phosphatase inhibitors is described in the Examples section hereinbelow. The utility of phosphatase inhibitors in the present invention may be evaluated using the animal fear conditioning/extinction and clinical experimental protocols disclosed in PCT Application No. WO02/078629, which is hereby incorporated by reference, with the exception that a phosphatase inhibitor is used instead of the pharmacological agent used therein.

The phosphatase inhibitor may be peptidal or non-peptidal in nature; however, the use of a non-peptidal phosphatase inhibitor is preferred. In a preferred embodiment, the phosphatase inhibitor is a CNS-penetrant phosphatase inhibitor. In addition, for convenience the use of an orally active phosphatase inhibitor is preferred. To facilitate dosing, it is also preferred that the phosphatase inhibitor is a long acting phosphatase inhibitor. An especially preferred class of phosphatase inhibitors of use in the present invention are those compounds which are orally active and long acting. Representative phosphatase inhibitors of use in the present invention are fully described, for example, in U.S. Pat. Nos. 3,929,992; 4,894,366, 5,431,896; 5,208,228; 5,190,950; 5,532,248; 5,250,678; 5,565,560; 5,693,648; 5,247,076; 5,344,925; 5,252,732; 5,349,061; 5,550,233; 5,310,903; 5,091,389; 5,324,659; 5,318,895; 5,258,389; 5,310,901 which are hereby incorporated by reference. Specific phosphatase inhibitors include, but are not limited to, okadaic acid, sodium orthovanadate, NaVa4, cnataridin, 1 naphthyphosphate sodium salt, $Na_3$, $VO_4$, NaF, b-glycerphosphate, $SC\alpha\alpha\delta9$ (Sigma), rapamycin and tacrolimus.

In one embodiment, the cell becomes stimulated prior to contacting the cell with the ERK activating agent. In another embodiment the cell becomes stimulated at the same time the cell is contacted with an ERK activating agent. In another embodiment, the cell becomes stimulated subsequent to contact with the ERK activating agent.

In one embodiment, methods of upregulating IL-10 production above that in resting cells in a macrophage-like cell comprising contacting said cell with a composition comprising an ERK activating agent in combination with a transcription factor or transcription factor mimic are provided. This method is advantageous as treatment with the combination to upregulate IL-10 can be effected prior to an inflammatory stimulus because the transcription factor mimic, especially mimics of Sp1 and/or STAT3 can supply the trigger for the second stimulus normally provided upon inflammatory insult. As such the combination can be used in preventative and/or prophylactic treatment regimens.

As used herein, "transcription factor" refers to any protein or modified form thereof that is involved in the initiation of transcription but which is not itself a part of the polymerase.

Transcription factors are proteins or modified forms thereof, which interact preferentially with specific nucleic acid sequences, i.e., regulatory elements. Some transcription factors are active when they are in the form of a monomer. Alternatively, other transcription factors are active in the form of oligomers consisting of two or more identical proteins or different proteins (heterodimer). The factors have different actions during the transcription initiation: they may interact with other factors, with the RNA polymerase, with the entire complex, with activators, or with DNA. Transcription factors usually contain one or more transcription regulatory domains.

"Transcription Factor Mimics" Factors that mimic the activity of transcriptional regulatory proteins such as gene-specific activators.

The invention further comprises identifying an ERK activating agent comprising contacting a cell with a test agent and measuring the effect that the test agent has on the activity and/or levels of ERK in the cell. Those test compounds that are capable of enhancing or activating the activity and/or levels of ERK in the cell are referred to herein as "ERK activating agents" Optionally, the method further comprises assaying the effect an ERK activating agent has on the induction of IL-10 in a stimulated cell. Preferred ERK activating agents are those agents capable of upregulating IL-10 production in a stimulated cell.

As used herein, terms like "enhancing" or "activating" with respect to ERK levels or activity means an increase in the levels or activity of ERK in a cell in the presence of a test compound as compared to the levels or activity of ERK in the absence of a test compound. Such increases may be at least two fold, but preferably at least about four fold or more, over the levels of ERK in the absence of a test agent. The elevated ERK levels should be rapidly induced and sustained for at least 30 minutes. ERK activating agents, as used herein with respect to IL-10 means an agent that increases the levels or production of IL-10 protein or gene expression. Such increases may be at least two fold, but preferably at least about four fold or more, over the levels of IL-10 in the absence of an ERK activating agent. The elevated IL-10 levels should be rapidly induced, reaching increased levels in less than an hour and sustained for at least 30 minutes.

As use herein terms like "upregulating" with respect to the levels of IL-10 production in stimulated cells is meant an increase in IL-10 production in a stimulated cell in the presence of an ERK activating agent as compared to the levels of IL-10 production in stimulated cells in the absence of an ERK activating agent. Such increase may be at least about two fold, preferably at least about four fold, preferably at least about five fold and even more preferably at least about eight fold over the levels of IL-10 production level of stimulated cells in the absence of an ERK activating agent. The cell may be stimulated prior to, simultaneously with, or subsequently to, contact with the ERK activating agent.

As used herein an "inflammatory stimulus" is any agent or condition that induces production of proinflammatory cytokines such as TNFα, IL-1, IL-6 and IL-12 by activating NF-kB and p38 in a responsive cell. An inflammatory response is characterized by secretion of one or more inflammatory molecules by a responsive cell. The inflammatory stimulus which acts on susceptible cells to secrete these molecules includes but is not limited to bacteria or components from bacteria, including but not limited to bacterial cell walls such as lipopolysaccharide (LPS) or lipotechoic acid (LTA). A cell susceptible to an inflammatory stimulus is herein considered a macrophage-like cell. A macrophage or other cell susceptible to an inflammatory stimulus and that has been acted upon by an inflammatory stimulus is said to be "stimulated". Cells that respond to inflammatory stimuli include but are not limited to, macrophages, leukocytes and dendritic cells.

In a preferred embodiment of the invention, the ERK activating agent is an agonist that interacts with a component of the ERK MAPK pathway and causes rapid and enhanced activation of the ERK pathway in a cell. In turn, activation of ERK by an ERK agonist in a stimulated cell will cause upregulation of IL-10 production by the stimulated cell.

Assays, particularly high throughput assays, may be adapted for use in the screening methods of the present invention. For general information on high-throughput screening, see, for example, *Cost-Effective Strategies for Automated and Accelerated High-Throughput Screening*, IBCS Biomedical Library Series, IBC United States Conferences, 1996; Devlin (Editor), *High Throughput Screening*, Marcel Dekker 1998. High throughput assays utilize one or more different assay techniques. For example, potential anti-inflammatory compounds are tested for their ability to activate ERK. These compounds are added to a test cell, such as a macrophage-like cell line in the presence of low levels of a stimulus, such as LPS (1 ng/ml). If the compounds are able to activate ERK in the presence of a stimulus, then the cells will make high levels of IL-10, which are measured by ELISA. These results may be confirmed by western blot analysis. An example of a representative high throughput assay is described in more detail in Example 4, below.

In one preferred embodiment of a high throughput screen for ERK activators, Applicants take advantage of the fact that activated ERK can phosphorylate a transcription factor, called Elk. Phosphorylated Elk drives the transcription of genes that have an Elk binding site in their promoter. Thus Applicants screen for Elk-mediated gene transcription to detect ERK activators. In the actual screen, the gene that is transcribed is luciferase, because it is easy to detect. Rather than place an Elk binding domain upstream of luciferase, a yeast transcription factor binding domain is used instead. Then, instead of using intact Elk, Applicants use a construct encoding a fusion protein, consisting of the transcriptional activation domain of Elk and a yeast transcription factor DNA binding domain. Thus, ERK activation leads to the phosphorylation of the Elk portion of the fusion protein, which binds to the DNA upstream of the luciferase reporter gene. Activation of luciferase in reporter cells means that ERK has been activated. The details of such an assay are given in the Examples.

Figure 9A:
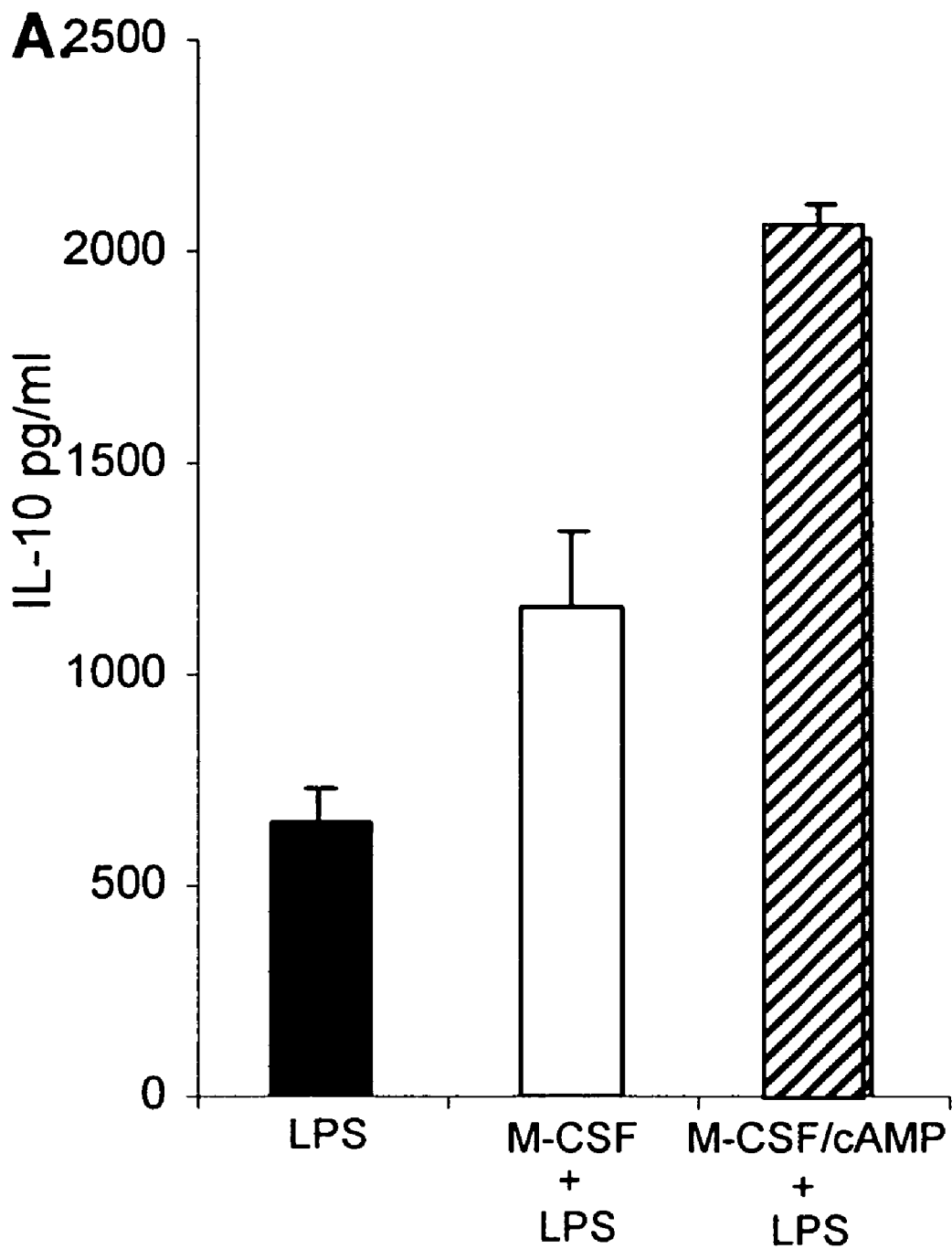
FIG. 9A is a graph of the ELISA determination of IL-10, levels in the supernatants of (BMMφ) that had been stimulated with LPS alone, or LPS plus colony stimulating factor 1 (CSF-1) or CSF-1 plus 8Br-cAMP LPS, and IgG simultaneously.
Figure 9B:
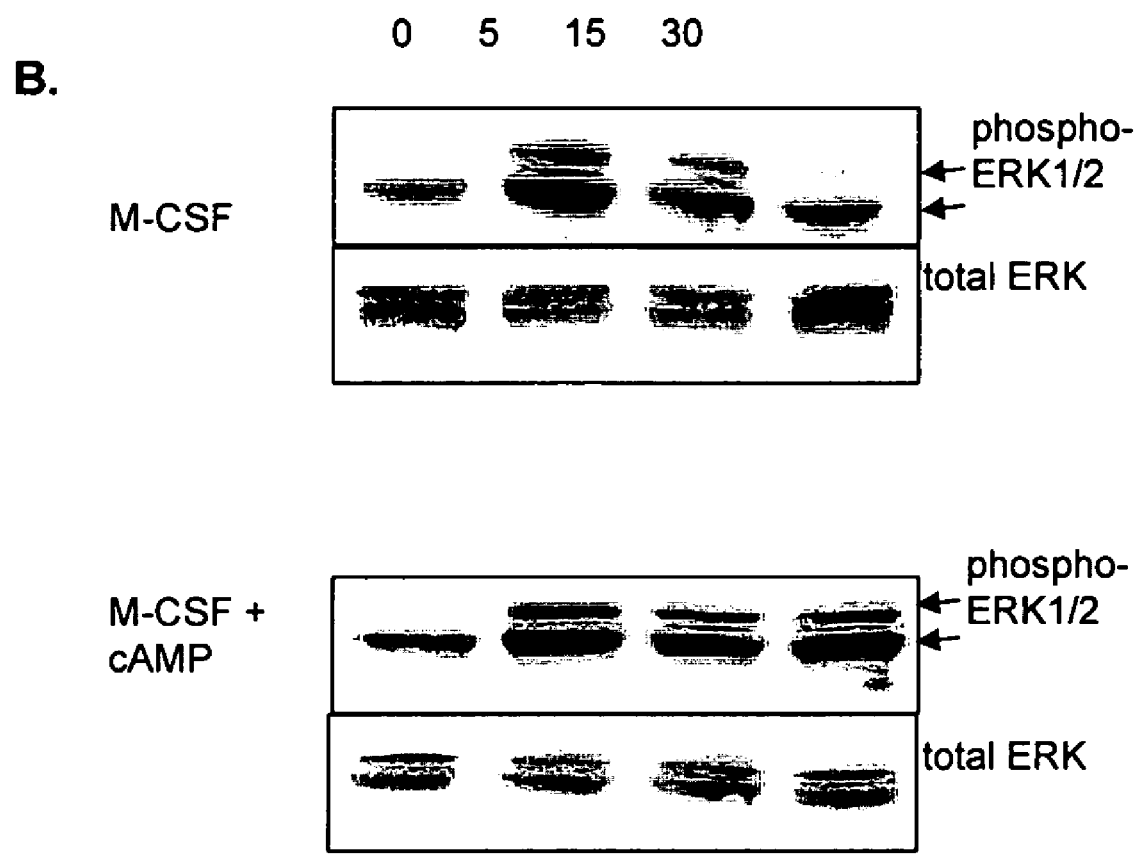
FIG. 9B is a Western Blot showing ERK activation in BMMφ stimulated with LPS alone, or LPS plus CSF-1 or LPS plus 8Br-cAMP.

In one preferred embodiment, an ERK activating agent identified by the screening method of the invention is colony stimulating factor-1 (CSF-1). CSF-1 causes upregulation of IL-10 in stimulated cells such as stimulated macrophages. FIG. 9B shows the activation of ERK by CSF-1. FIG. 9A shows IL-10 induction in the presence of an inflammatory stimulus (bacterial cell walls or LPS).

The ERK activating agents identified in accordance with the screening methods of the invention may be used to enhance the production of IL-10 in a patient in need treatment for inflammation. Such situations include those conditions having proinflammatory components including but not limited to acute sepsis, endotoxemia and related conditions. Other situations include those associated with inflammation related to autoimmune diseases including, but not limited to, moderately acute autoimmune disorders such as Kawasaki Disease; and chronic autoimmune disorders such as SLE, rheumatoid arthritis, inflammatory bowel disease, Sydenham's chorea (post Streptococcal), and autoimmune hemolytic anemia.

Other specific examples of inflammatory conditions treatable according to the invention include, but are not limited to, anaphylaxis; drug sensitivity; food sensitivity and the like; cutaneous inflammation such as dermatitis, eczema, psorisis, contact dermatitis, and the like; arthritis such as osteoarthritis, psoriatic arthritis, lupus, spondylarthritis and the like. Anti-inflammatory compounds are also useful for treating chronic pulmonary inflammatory diseases such as chronic obstruction pulmonary disease, cystic fibrosis, and allergic bronchopulmonary aspergillosis (ABPA). The anti-inflammatory compounds of the present invention may further be used to replace corticosteroids in any application in which corticosteroids are used including immunosuppression in transplants and cancer therapy.

As used herein the terms "treating" or "treatment" include i) prophylactic treatment of those patients susceptible to an inflammatory or proinflammatory immune response, ii) treatment at the initial onset of symptoms, and iii) treatment of ongoing or relapsing symptoms of inflammation and proinflammatory immune response. A "therapeutically effective amount" is an amount of modulating agent sufficient to prevent, diminish or eradicate symptoms of inflammation.

The ERK activating agents identified in accordance with the screens invention may be administered to a patient in therapeutically effective amounts and formulated as a pharmaceutical composition, a sterile aqueous or non-aqueous solution, or a suspension or emulsion, which additionally comprises a physiologically acceptable carrier (i.e., a non-toxic material that does not interfere with the activity of the active ingredient). Any suitable carrier known to those of ordinary skill in the art may be employed in the pharmaceutical compositions of this invention. Representative carriers include physiological saline solutions, gelatin, water, alcohols, natural or synthetic oils, saccharide solutions, glycols, injectable organic esters such as ethyl oleate or a combination if such materials. Optionally, a pharmaceutical composition may additionally contain preservatives and/or other additives such as, for example, antimicrobial agents, anti-oxidants, chelating agents and/or inert gases.

Routes and frequency of administration of a modulating agent of the invention will vary from patient to patient. In general, the pharmaceutical compositions may be administered orally, intravenously, intraperitoneally, intramuscularly, subcutaneously, pulmonary, or transdermally. A suitable dose is an amount of modulating agent that is sufficient to show improvement in the symptoms of a patient in need of inhibition of a proinflammatory immune response and inflammation. Such improvement may be detected based on a determination of relevant cytokine levels (e.g. IL-1, IL-6, IL-10 or IL-12) levels, by monitoring inflammatory responses or through an improvement in clinical symptoms associated with the disease or inflammatory condition.

For example, therapeutically effective amount of an anti-inflammatory compound of the invention (i.e., an effective dosage) may range, from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an anti-inflammatory compound of the invention can include a single treatment or, preferably, can include a series of treatments. In one example, a subject is treated with an anti-inflammatory compound of the invention in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of an anti-inflammatory compound of the invention used for treatment may increase or decrease over the course of a particular treatment.

In one embodiment of the invention, a person suffering from an inflammatory or proinflammatory condition may be treated with a cotherapeutic treatment regimen comprising an ERK activating agent of the invention and another agent that modulates a particular pathological process, condition or disease state. As used herein a "co-therapeutic treatment regimen" means a treatment regimen wherein two or more drugs are administered simultaneously or sequentially, separated by minutes, hours or days, but in some way act together to provide the desired therapeutic response. In one preferred embodiment of a co-therapeutic treatment regimen of the invention, a person suffering from septic shock, endotoxemia, bacteremia or the like, may be treated with an ERK activator, such as CSF-1 in combination with an antibiotic.

In another preferred embodiment of a co-therapeutic treatment regimen of the invention, a person suffering from septic shock, endotoxemia, bacteremia and the like, may be treated with an ERK-activating agent, in combination with an agent that inhibits cellular phosphatases, for example okadaic acid, phenylarsine oxide, calyculin, or vanadate.

Figure 11:
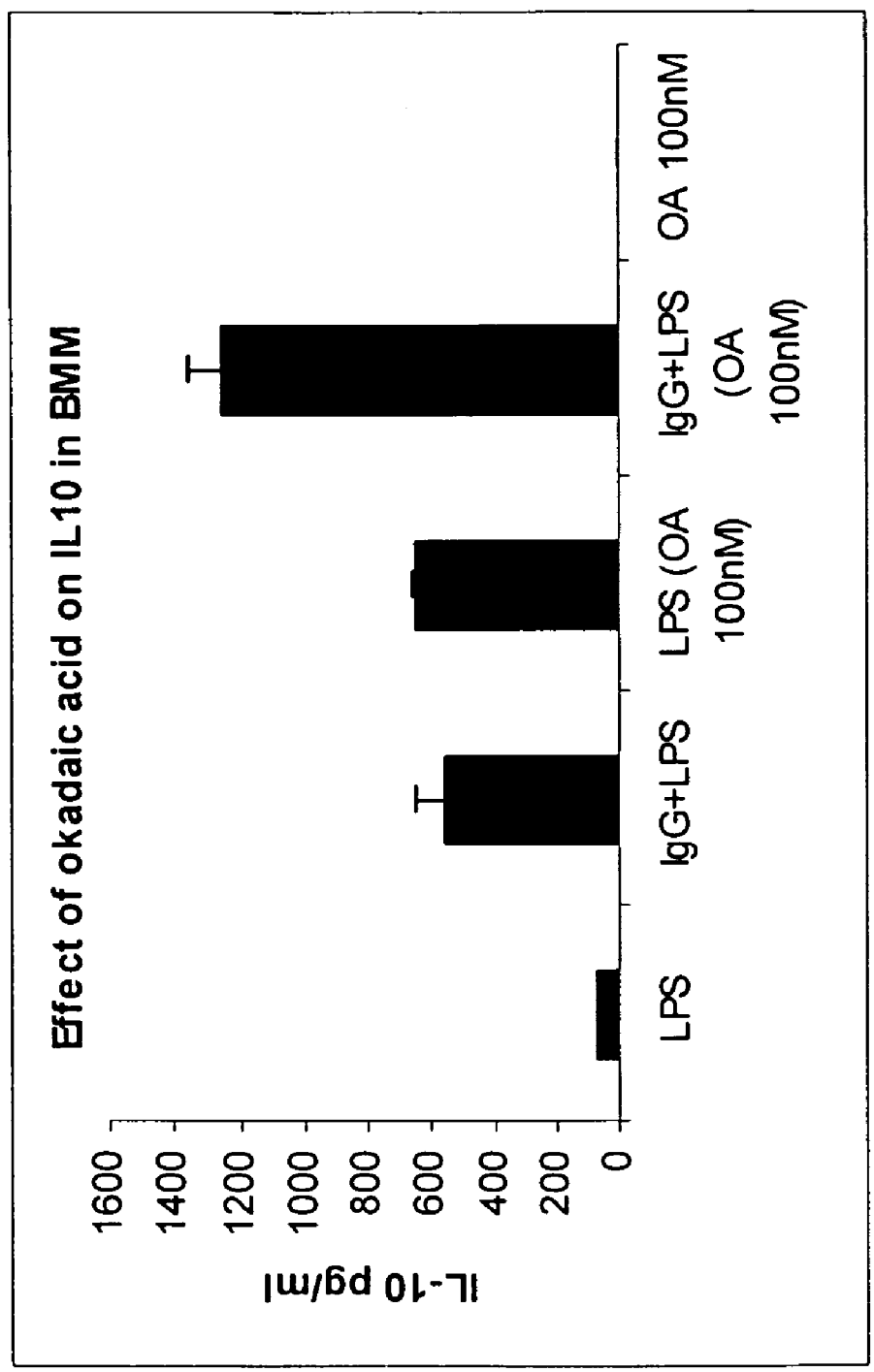
FIG. 11 is a graph showing IL-10 production after treating macrophages with okadaic acid to inhibit cellular phosphatases. Macrophages were pretreated with 100 uM okadaic acid for 1 hour and then stimulated with LPS plus or minus E-IgG.
Figure 12:
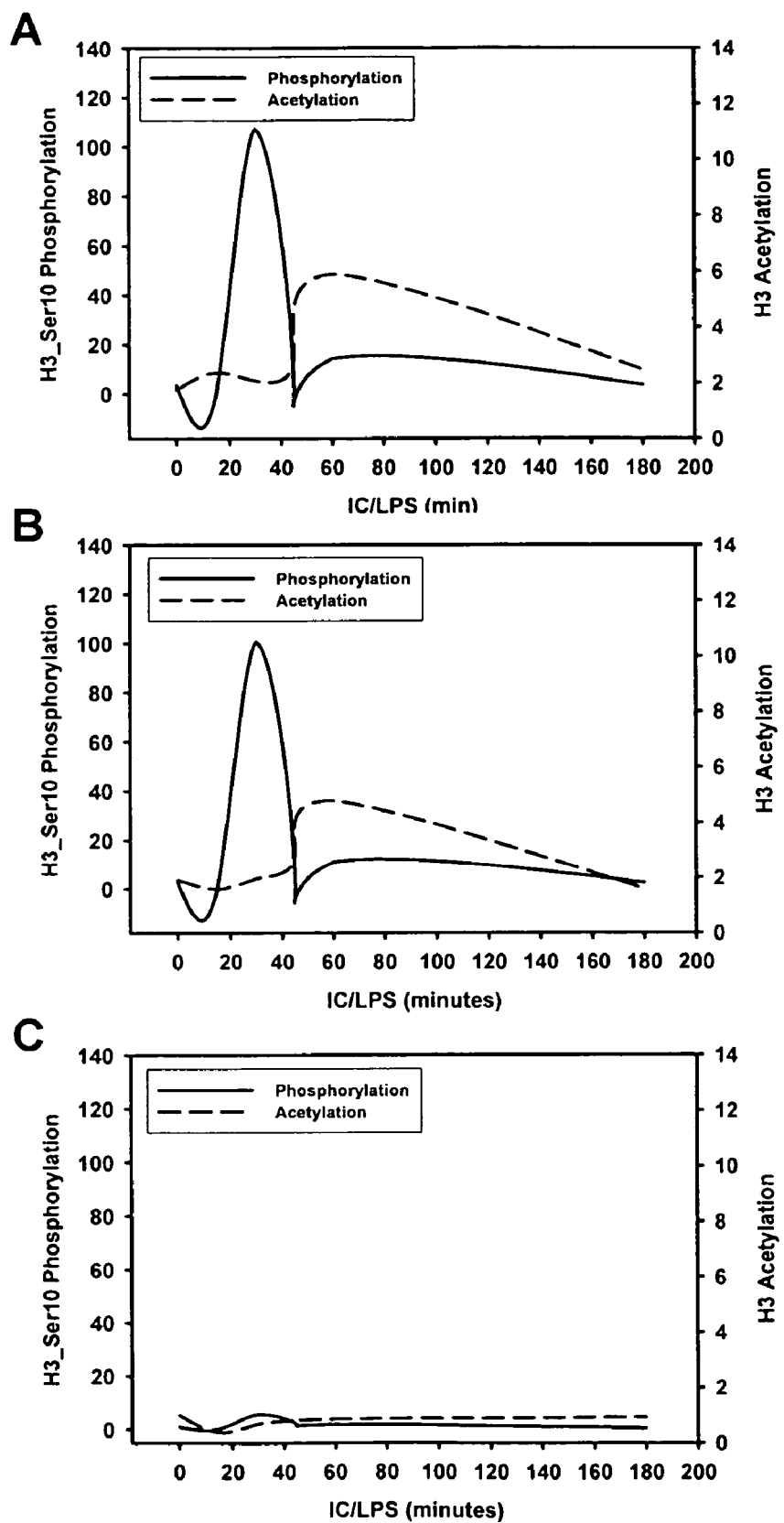
FIG. 12A-C are graphs showing dynamic changes in histone modifications at the il-10 promoter region. Quantitative real-time PCR analysis of three regions of the murine IL-10 (mIL-10) promoter was performed following ChIP assays using antibodies to either acetylated or phosphorylated histone H3. The fold change in each case is presented as a comparison of the experimental sample at each time relative to a corresponding control sample precipitated with normal rabbit serum. H3 Ser10 phosphorylation is designated by the left y-axis. H3 acetylation is designated by the right y-axis. Each sample was quantitated in duplicate on two separate occasions. (A) Histone H3 association with the Sp1 binding site of the mIL-10 promoter region located −294 and −73 (B) Histone H3 association with the STAT3 binding site of mIL-10 proximal promoter region located −704 and −603 (C) Histone H3 association with mIL-10 5'-flanking region located between −1563 and −1427.
Figure 13:
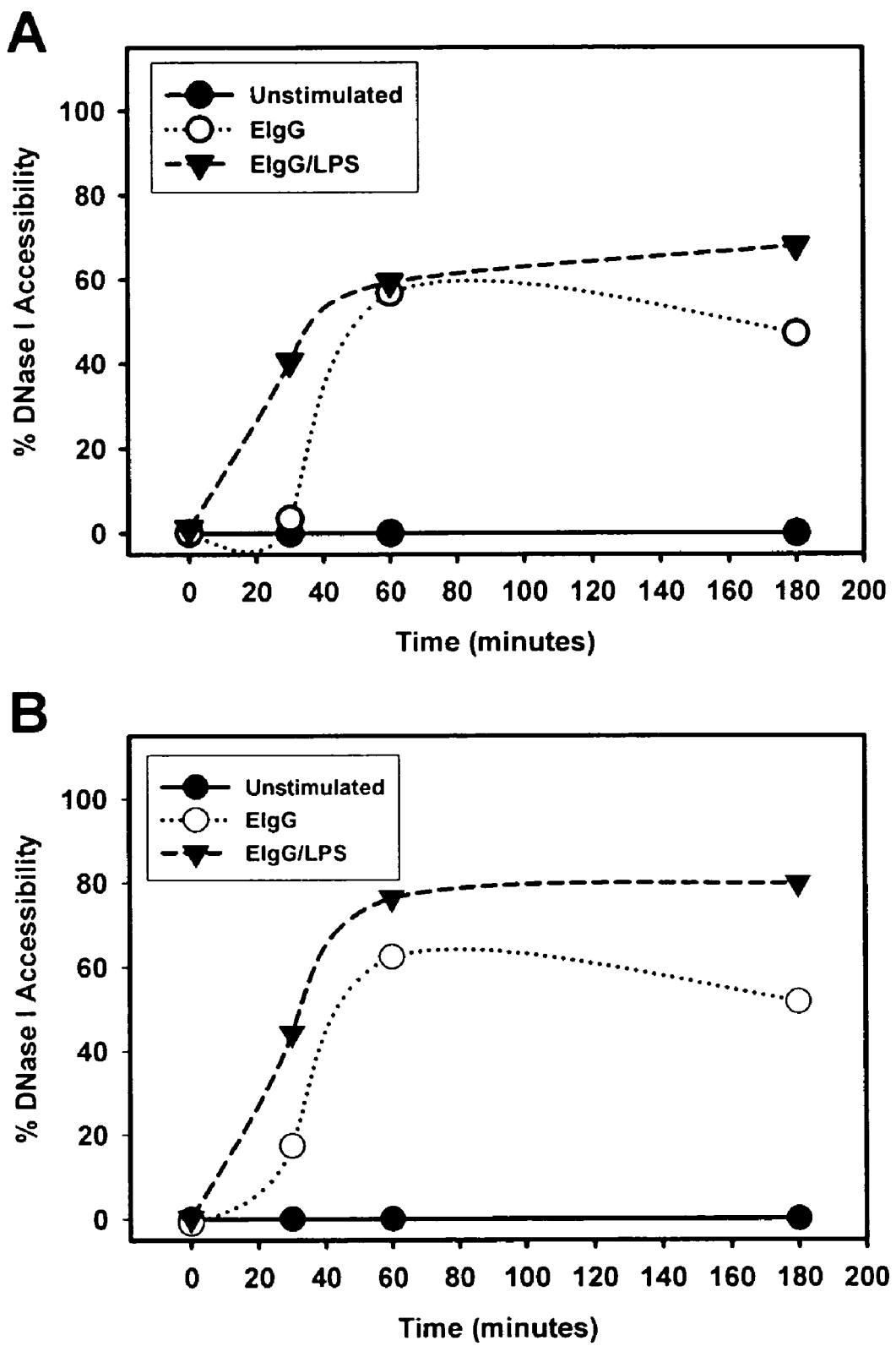
FIG. 13 A-B are graphs showing changes in DNase I accessibility at the mIL-10 promoter region. Quantitative real-time PCR analysis was performed on two regions of the mIL-10 promoter following brief exposure of nuclei to DNase I. Macrophages were stimulated with E-IgG alone (open circles) or in combination with LPS (closed triangles) and compared to unstimulated cells (closed circles). Cells were analyzed at various times post-stimulation and expressed as % accessibility, as described in Materials and Methods. (A) Changes of DNase I accessibility of the Sp1 binding region mIL-10 promoter located between −294 and −73; (B) Changes of DNase I accessibility of the STAT3 binding region of the mIL-10 promoter located between −704 and −603.

While not being limited to any one theory, the inventors believe that the mechanism of IL-10 induction and superinduction is the activation of ERK (in the presence of stimulus) which leads to chromatin modifications at the IL-10 locus to make the promoter more accessible to transcription factors that bind it. ERK acts by phosphorylating the chromatin around the IL-10 gene to make it more accessible to transcription factors that are induced by inflammation via NF-kB and p38. One way to enhance the the ERK effect is to prolong this phosphorylation by preventing the dephosphorylation of the chromatin. Thus, ERK phosphorylates the chromatin and cellular phosphotases dephosphorylate the chromatin to return it to baseline levels. FIG. 11 shows that Okadaic Acid, an inhibitor of cellular phosphatases, dramatically increases IL-10 production in stimulated BMMφ. FIGS. 12 and 13 show changes in histone modifications at the IL-10 promotor and changes in DNase I accessibility at the mIL-10 promoter region.

In yet another aspect of the invention, the invention provides ERK inhibiting agents. Such inhibiting agents are preferably antagonists of the ERK MAPK pathway and cause rapid inhibition of the ERK pathway in a cell. In turn, inhibition of the ERK pathway will cause inhibition of IL-10 production in a stimulated cell. The inhibition of IL-10 production in a cell is useful for enhancing the immune response to a stimulus such as a microbe and is preferably used as an adjunct to antibiotic therapy.

High throughput assays may be used to identify antagonists in accordance with the invention. In one example a suitable assay comprises contacting a test cell such as a macrophage-like cell line with a potential antagonist of ERK in the presence of a strong IL-10 stimulus, such as low levels of LPS and immune complexes. If the potential antagonist inhibits ERK, then the cells would make little or no IL-10 as measured by standard assays such as ELISA. The ERK antagonists identified in accordance with screening methods of the invention may be used to inhibit the production if IL-10. These agents may be useful as adjunctive therapies to treat infectious diseases where high IL-10 levels predispose the host to fulminent infection. These diseases include but are not limited to visceral leishmaniasis and lepromatous leprosy.

Such ERK antagonists identified in accordance with the invention may be administered to a patient in therapeutically effective amounts and formulated as pharmaceutical compositions as described earlier.

EXAMPLES

Example 1

ERK Activation Following FcγR Ligation Leads to Chromatin Modifications at the IL-10 Locus Mice. 6 to 8 week-old BALB/c mice were purchased from Takonic (Germantown, N.Y.). All mice were maintained in HEPA-filtered Thoren units (Thoren Caging Systems, Inc., Hazleton, Pa.) at the University of Maryland, College Park. Mice were used at 6-10 weeks of age as a source of bone marrow derived macrophages (BMMφ).

Reagents. The p38 MAPK inhibitor, SB203580, and the MEK/ERK inhibitor, PD98059, were purchased from Calbiochem (La Jolla, Calif.). The JNK inhibitor peptide I was purchased from Alexis (San Diego, Calif.). Washed sheep erythrocytes (SRBC) were purchased from Lampire (Pipersville, Pa.). Rabbit IgG antibody to SRBC (αSRBC-IgG) was purchased from Cappel (Durham, N.C.). Ultra pure LPS from *E. coli* K12 strain was obtained from InvivoGen (San Diego, Calif.). Anti-phospho-H3 and acetyl-H3 antibodies and ChIP assay kits were purchased from Upstate (Lake Placid, N.Y.). Anti-p38 (phospho-T180/Y182), anti-STAT3 and anti-Sp1 antibodies were purchased from Abcam, Inc, (Cambridge, Mass.). Anti-p38 (total), anti-ERK1/2 (total and phospho-T202/Y204) and anti-JNK (phospho-T183/Y185) were purchased from Cell Signaling Technology, Inc, (Beverly, Mass.).

Cells. Bone marrow derived macrophages were prepared as described previously (Anderson, C. F. and D. M. Mosser. 2002. *J. Immunol.* 168:3697-3701). Briefly, bone marrow was flushed from the femurs and tibias of mice and cells were plated in petri dishes in DMEM/F12 supplemented with 10% FBS, penicillin/streptomycin, glutamine, and 10% conditioned medium from the supernatant of M-CSF secreting L929 fibroblasts (LCM). Cells were fed on day 2, and complete media was replaced on day six. Cells were used at 7 to 10 days for experiments. The RAW264.7 macrophage cell line (American Type Culture Collection, Manassas, Va.) was maintained in RPMI supplemented with 10% FBS, penicillin/ streptomycin and glutamine (Gibco Invitrogen Corp., Carlsbad, Calif.).

Figure 7:
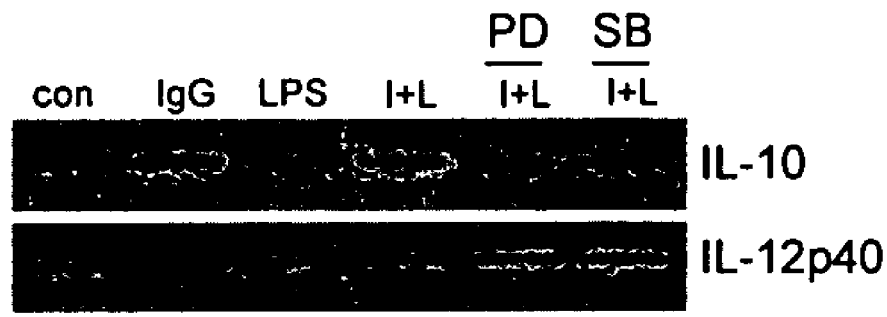
FIG. 7 A-B shows that inhibition of ERK blocks histone H3 phosphorylation at the IL-10 promoter in stimulated BMMφ. Cells were pretreated with PD98059 (10 μM), SB203580 (1 μM) or medium for 30 min then stimulated with medium (open bar), IgG-OVA (dotted bar), LPS (solid bar), or both (striped bars) for 40 min. ChIP analysis was carried out using a phospho-H3 specific Ab. A. Conventional RT-PCR was carried out using IL-10 promoter or IL-12p40 promoter specific primers. B. Real time PCR analysis of samples obtained in A. Samples were normalized to input DNA controls.
Figure 7:
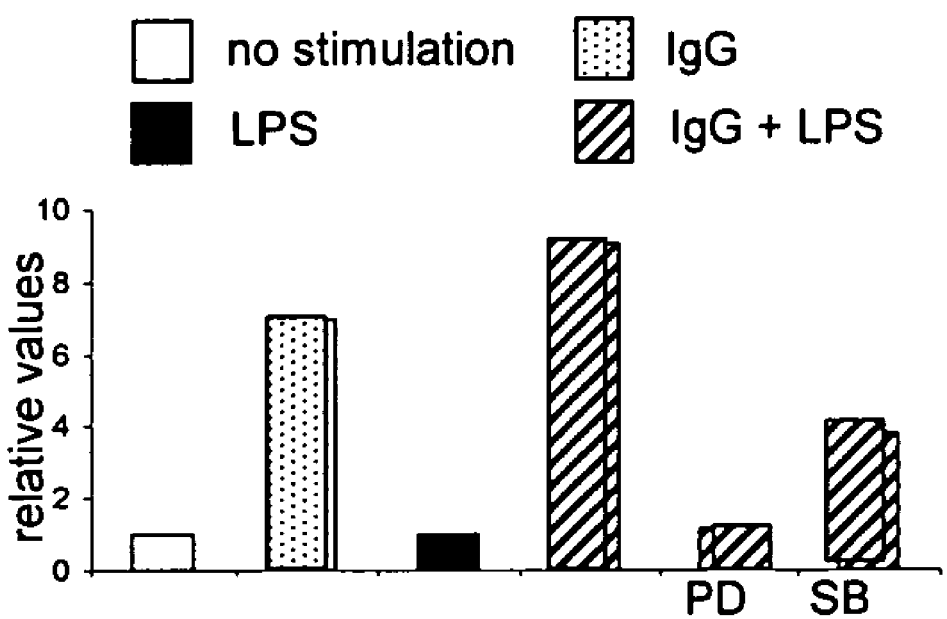

Opsonization of erythrocytes. IgG-opsonized erythrocytes (E-IgG) were generated by incubating SRBC with αSRBC-IgG at nonagglutinating titers for 30 min at room temperature while rotating. Opsonized cells were washed once in HBSS (Gibco BRL, Gaithersburg, N.C.) and resuspended in complete media. E-IgG were added to macrophages at a ratio of 10 E-IgG: 1 Mϕ. For some experiments (FIG. 7) IgG-OVA was used as the immune complex. IgG-OVA was prepared as previously described (Anderson, C. F. and D. M. Mosser. 2002. *J. Immunol.* 168:3697-3701).

Cell stimulation assays. For cytokine analysis, $3\times10^5$ macrophages per well were plated overnight in a 48-well plate in DMEM/F12. Cells were then washed and activated with either 10 ng/ml LPS alone or in combination with either a 10:1 ratio of E-IgG. Supernatants were harvested approximately 20 h later. Cytokines were measured by ELISA using the following Ab pairs from BD Pharmingen (San Jose, Calif.): IL-12p40, C15.6 and C17.8; IL-10, JES5-2A5 and JES5-16E3; TNF-α, G281-2626 and MP6-XT22.

Generation of siRNA and cell transfections. To generate siRNA for p38α and ERK1, the silencer™ siRNA Construction Kit was used (Ambion, Austin, Tex.) following the manufacturers guidelines. The oligo sequences used to generate siRNA templates were: p38 sense AACTGGCACTTCAC-GATCCTGCCTGTCTC (SEQ ID NO: 3), antisense AACAGGA TCGTGAAGTGCCAGCCTGTCTC (SEQ ID NO: 4); ERK1 sense ACTTGATGGCCACTCTGGTC CCT-GTCTC (SEQ ID NO: 5), antisense AAGACCAGAGTGGC-CATCAAGCCTGTCTC (SEQ ID NO: 6). For cell transfections, $5\times10^6$ primary BMMϕ were transfected on day 6 with 100 nM of siRNA using the Amaxa Nucleofector™ system (Amaxa Inc., Gaithersburg, Md.) and stimulated 48 h later. Gene silencing was confirmed by Taqman real time PCR using the following primer sequences: p38 sense CAG-GATCGTGAAGTGCCAGAA (SEQ ID NO: 7), antisense GCCCTCGGAGGATCTGGTA (SEQ ID NO: 8); ERK1 sense TGTTATAGGCATCCGAGACATCCT (SEQ ID NO: 9), antisense CCATGAGGTCCTGAACAATGTAAAC (SEQ ID NO: 10).

Western blots. $2\times10^6$ BMMϕ per well were plated overnight in 60 mm culture dishes. Cells were then washed and activated with 10 ng/ml LPS alone or in combination with E-IgG in a final volume of 1 ml DMEM/F12 without L929 condition media. Cells were then lysed in ice cold lysis buffer (100 mM Tris, pH8, 2 mM EDTA, 100 mM NaCl, 1% Triton X-100 containing Complete EDTA-free protease inhibitor cocktail (Roche Diagnostics Corp., Indianapolis, Ind.), 1 mM sodium vanadate, 50 mM sodium fluoride, and 1 mM PMSF and left on ice for 30 min. Lysates were then cleared by centrifugation (13 Krpm, 10 min, 4° C.). Equal amounts of protein were loaded onto 12% SDS-polyacrylamide gels. After separation, protein was transferred to PVDF membrane for 2 h. Membranes were then blocked with 5% milk powder in TBS-Tween (0.1%) for 1 h at room temperature, washed briefly and incubated with primary antibodies (1:1000 in 5% BSA in TBS-Tween) overnight at 4° C. Membranes were washed and incubated with secondary antibody (1:5000) for 1 h at room temperature and visualized using Lumi-Light-PLUS chemiluminescent substrate (Roche Diagnostics Corp., Indianapolis, Ind.).

Electrophoretic mobility shift assay (EMSA). Nuclear extracts were prepared from $2\times10^7$ Mϕ using the Nuclear Extraction kit (Panomics, Redwood City, Calif.) following the manufactures protocol. EMSAs were carried out using the EMSA "Gel-Shift" kit (Panomics, Redwood City, Calif.). Briefly, 5 μg of nuclear extract were incubated with biotin-Sp1 or STAT3 probe±unlabelled probe for 30 min at 20° C., and then run on a 6% polyacrylamide gel. Oligo/protein complexes were transferred to Biodyne B membrane (Pall, Ann Arbor, Mich.). Following transfer, membranes were incubated with streptavidin-HRP and protein visualized by chemiluminescence.

Luciferase assay. RAW264.7 macrophages ($4\times10^6$) were transfected with 5 μg pGL-IL10-luciferase reporter plasmid (Brightbill, H. D., et al. 2000. *J. Immunol.* 164:1940-1951) (a generous gift of Dr Stephen Smale, Howard Hughes Medical Institute, University of California, Los Angeles, Calif.) with the Amaxa Nucleofector™ system. After transfection, $3\times10^5$ cells were plated per well in 48-well culture plates. After 24 h, cells were washed and stimulated as described in Cell stimulation, then lysed using Glo-Lysis™ Buffer and luciferase activity measured using the Bright-Glo™ Luciferase system (Promega, Madison, Wis.).

Chromatin immunoprecipitation (ChIP). ChIPs were carried out using the ChIP Assay kit following the manufacturer's protocol (Upstate USA, Inc., Lake Placid, N.Y.). Briefly, $1\times10^6$ BMMϕ were plated overnight in 6-well plates. Cells were stimulated as described in Figure Legends then fixed for 10 min at 37° C. in paraformaldehyde (1% final concentration). Cells were washed on ice with ice cold HBSS containing 1 mM PMSF, harvested and then lysed in SDS Lysis buffer. DNA was sheared by ultrasonication using a High Intensity Ultrasonic Processor (Cole-Parmer Instrument Co., Vernon Hills, Ill.), $3\times10$ s pulses, 20% amplitude. Lysates were cleared by centrifugation and diluted in ChIP dilution buffer. Lysates were precleared using salmon sperm DNA/Protein A agarose and a sample of 'input DNA' collected at this point. Protein/DNA complexes immunoprecipitated with 5 μg of antibody overnight at 4° C. Antibody/protein/DNA complexes were then captured using salmon sperm DNA/Protein A agarose for 1 h at 4° C. After washing beads with low and high salt, LiCl and TE buffers, the protein/DNA complexes were eluted using 1% SDS, 0.1 M NaHCO$_3$ buffer and disrupted by heating at 65° C. for 4 hours. DNA was then extracted using phenol/chloroform extraction and ethanol precipitation. PCR was carried out using promoter specific primers; IL-10 promoter (Sp1 binding region −294 to −73); sense CAGCTGTCTGCCTCAGGAAATACAA (SEQ ID NO: 11), antisense TATTCAGGCTCCTCCTCCCTCTTCT (SEQ ID NO: 12) (94° C., 15 s; 60° C., 30 s; 72° C., 1 min, 35 cycles), IL-10 promoter (STAT3 binding region −649 to −448); sense TCATGCTGGGATCTGAGCTTCT (SEQ ID NO: 13), antisense CGGAAGTCACCTTAGCACTCAGT (SEQ ID NO: 14) (94° C., 15 s; 56° C., 30 s; 72° C., 1 min, 35 cycles) IL-12p40 promoter; sense CAAATCTGGGAG-GCAGGAAAC (SEQ ID NO: 15), antisense CAAAG-CAAACCTTTCTATCAAATACACA (SEQ ID NO: 16) (94° C., 15 s; 56° C., 30 s; 72° C., 1 min, 35 cycles). The above numerical designations of IL-10 promoter sequence are made according to Genbank accession number M84340. PCR products were separated on 2% agarose gels. For relative quantization of promoter levels, real time PCR was performed as described below.

Real time PCR. Real time PCR was carried out with the ABI Prism 7700 Sequence Detection System using SYBR Green PCR reagents (Applied Biosystems, Foster City, Calif.) following the manufactures guidelines. Melting curve analyses were performed after PCR amplification to ensure that the single product with the expected melting curve characteristics was obtained. In addition to the primers used for IL-10 ChiP assays (IL-10 primers used were: sense CCA-CAAAGCCTTGCA (SEQ ID NO: 1), antisense AGTAA-GAGCAGGCAGCATAGCA (SEQ ID NO: 2)) one additional pair of primers for the control element located −1563 to −1427 was used: sense 5'-CAGTCAG-GAGAGAGGGCAGTGA-3' (SEQ ID NO: 17) and antisense 5'-TTTCCAACAGCAGAAGC AAC-3' (SEQ ID NO: 18).

DNase I sensitivity assayed by Real-time PCR. DNase I accessibility was determined as previously described (Goriely, et al. 2003. *Blood* 101:4894-4902; Rao, et al. 2001. *J. Immunol.* 167:4494-4503.) with minor modifications. Briefly, cells grown in 100 mm tissue culture dishes were stimulated at different time intervals, and formaldehyde was added for 15 min at RT at a final concentration of 1%. Glycine (0.125 M) was added to neutralize formaldehyde. Cells were washed and lysed in 4 ml of ice-cold Nuclei EZ lysis buffer (Sigma, Saint Louis, Mo.). Cells were scrapped into conical tube, centrifuged at 500 ×g for five minutes, and the nuclei were resuspended with an additional 4 ml of ice-cold Nuclei EZ lysis buffer. Washed nuclei were pooled and resuspended in ice-cold DNase I buffer (100 mM NaCl, 50 mM Tris of pH 8.0, 3 mM $MgCl_2$, 0.15 mM spermine, and 0.5 mM spermidine) supplemented with 1 mM $CaCl_2$. DNase I (Roche Diagnostics, Indianapolis, Ind.) was then added and incubated at 37° C. for 2 minutes. The reaction was stopped by adding equal volume of DNase I stop buffer (containing 10 mM EDTA, 20% SDS, and 0.4 M NaCl) and incubated at 65° C. for 4 hrs to reverse cross-links. Proteinase K (100 μg) and RNase A (10 μg) were then added at 37° C. overnight. DNA was purified with phenol/chloroform extraction and ethanol precipitation. Real-time PCR was carried out as previously described (Rao et al., supra and Crawford, et al. 2004. *Proc. Natl. Acad. Sci. U.S.A* 101:992-997).

Stimulation of macrophages in the presence of immune complexes results in the augmented activation of two MAPK, p38 and ERK. We examined the magnitude and kinetics of MAPK activation in BMMφ, following stimulation in the presence or absence of immune complexes. BMMφ were stimulated with LPS alone or in combination with E-IgG, and cells were lysed at various intervals thereafter and total protein extracts were analyzed by western blotting using phospho-specific antibodies against p38, ERK, or JNK. LPS stimulation alone resulted in relatively modest levels of MAPK activation, which peaked at 20 minutes and began to decline by 40 minutes (FIG. 1). The combination of E-IgG and LPS resulted in a rapid and prolonged activation of ERK (top) and p38 (middle). Both MAPKs were strongly phosphorylated within 5 minutes of stimulation. There was also an increase in the total amount of p38 and ERK phosphorylation, which persisted for 40 minutes (ERK) or longer (p38) (FIG. 1). The magnitude of JNK phosphorylation following LPS administration was not substantially increased by the addition of immune complexes (FIG. 1). In summary, compared to stimulation with LPS alone, stimulation of macrophages in the presence of immune complexes resulted in a more rapid and enhanced activation of ERK and p38, whereas LPS-induced JNK activation was not significantly increased by the addition of immune complexes.

Figure 2:
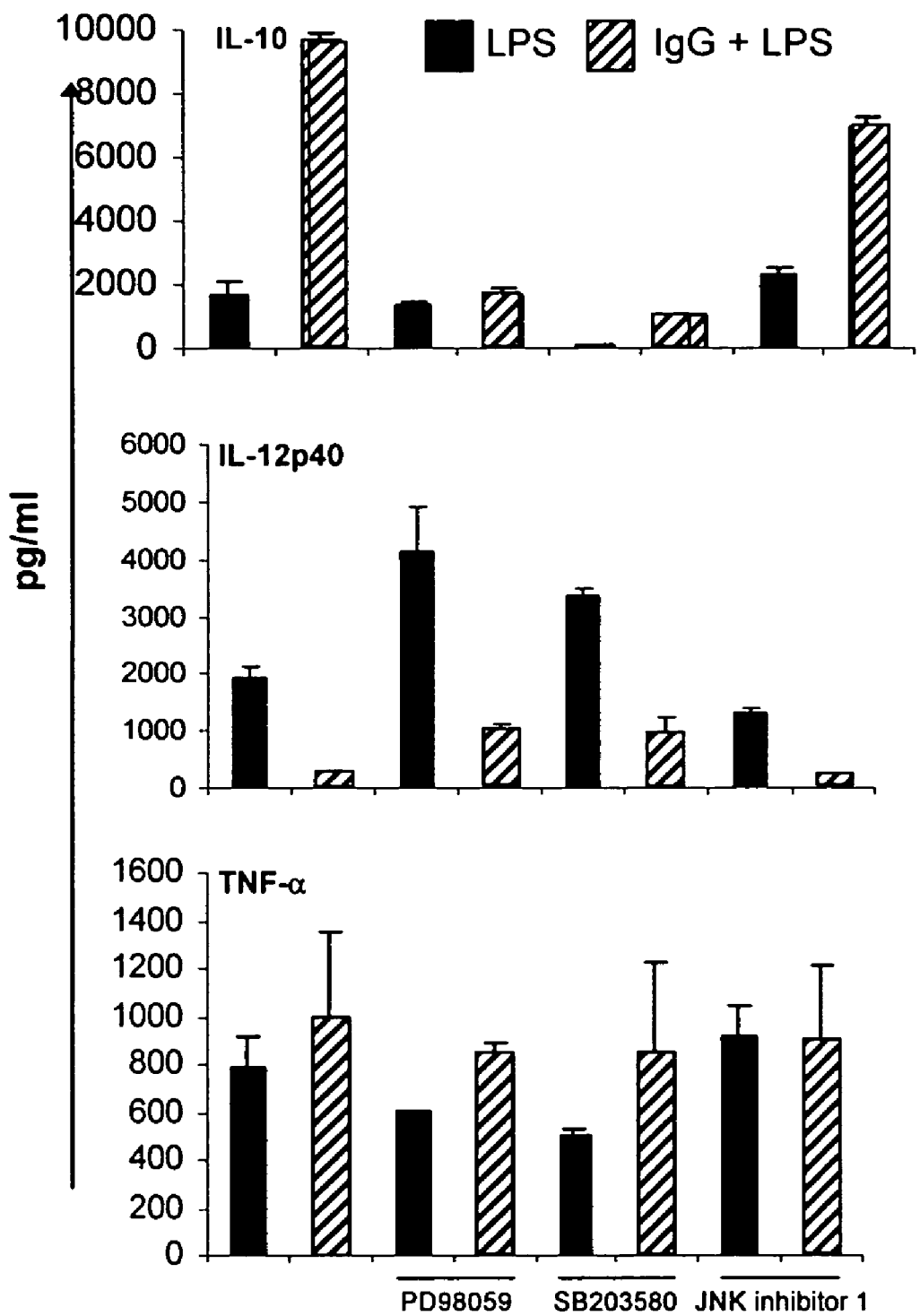
FIG. 2 is a graph of the enzyme-linked immunosorbant assay (ELISA) determination of IL-10, IL12p40 and TNF alpha in the supernatants of BMMφ exposed to inhibitors PD98059, SB203580, and JNK inhibitor 1, in the presence of lipopolysaccharide endotoxin (LPS) alone or LPS in combination with IgG. BMMφ were pretreated with PD98059 (10 μM) (ERK inhibitor), SB203580 (1 μM) (p38 inhibitor) or JNK inhibitory peptide (1 μM) (JNK inhibitor) for 30 min, then stimulated with LPS (10 ng/ml) alone (solid bars) or LPS+E-IgG (striped bars). Supernatants were harvested after 20 h and cytokines analyzed by ELISA. Data represent the mean+SD of triplicate samples and is representative of at least 4 individual experiments.

The role of MAPK activation in IL-10 induction. Due to the differences we observed in MAPK activation following stimulation in the presence of immune complexes, we examined the effect of inhibiting the 3 major MAPK on macrophage cytokine production. We previously demonstrated that the stimulation of IFN-γ-primed macrophages in the presence of immune complexes resulted in a dramatic increase in IL-10 production (Goriely, S., D. et al. 2003. *Blood* 101:4894-4902), and a decrease in the production of IL-12 (Sutterwala, F. S., et al. 1997. *J. Exp. Med.* 185:1977-1985). We show similar data in FIG. 2, using unprimed macrophages. Stimulation of macrophages with LPS alone resulted in the production of a modest amount of IL-10 (FIG. 2, solid bars), but coupling this stimulation with immune complexes, increased IL10 production by more than 5 fold, to nearly 10 ng/ml (FIG. 2, striped bars). The stimulation of these unprimed macrophages with LPS alone also induced the production of substantial levels of the p40 subunit of IL-12 (FIG. 2, middle panel, solid bars), and coupling this stimulation with E-IgG (striped bars) decreased IL-12 production to less than 200 pg/ml. Thus in this figure, stimulation of unprimed macrophages in the presence of immune complexes gives rise to a population of anti-inflammatory macrophages secreting approximately 10 ng/ml of IL-10 and less than 200 pg/ml of IL-12. We have previously used several different stimuli and a variety of immune complexes, both soluble and particulate, to achieve a similar reciprocal alteration in the production of these two cytokines (Gerber, J. S. and D. M. Mosser. 2001. *J. Immunol.* 166:6861-6868; Rao, S., et al. 2001. *J. Immunol.* 167:4494-4503).

Several recent studies have demonstrated a role for MAPKs in LPS signaling for cytokine secretion (Crawford, G. E., et al. 2004. *Proc. Natl. Acad. Sci. U.S.A* 101:992-997; Anderson, C. F. and D. M. Mosser. 2002. *J. Leukoc. Biol.* 72:101-106). To investigate the role of MAPKs in IL-10 induction, BMMφ were treated with specific pharmacological inhibitors of p38, ERK, or JNK prior to stimulation in the presence (striped bars) or absence (solid bars) of immune complexes (FIG. 2). Inhibition of either p38 with SB203580, or ERK with the MEK inhibitor PD98059, resulted in a substantial inhibition of IL-10 secretion (FIG. 2). Inhibition of p38 prevented the LPS-induced IL-10 production, whereas inhibition of ERK appeared to prevent the superinduction of IL-10 caused by immune complexes. Neither of these inhibitors decreased IL-12 production (FIG. 2, middle panel). In fact, IL-12 production was actually increased by the ERK inhibitor (PD98059), as previously reported (Guo, X., et al. 2003. *J. Biol. Chem.* 278:22237-22242). The decrease in IL-12 production caused by the addition of immune complexes was not affected by the inhibition of either ERK or p38. Inhibition of JNK, with the JNK inhibitor 1 peptide, had no effect on IL-10 production. This inhibitor did, however, partially inhibit IL-12p40 release. For these studies, TNF-α was used as a control cytokine, whose production was not reproducibly affected by any of the three MAPK inhibitors (FIG. 2, lower panel).

The addition of E-IgG alone to resting macrophages did not result in cytokine secretion (data not shown). Immune complexes alone, while they can modify chromatin by activating ERK, do not result in cytokine production. They must be coupled with an inflammatory stimulus in order to superinduce IL-10.

Figure 3:
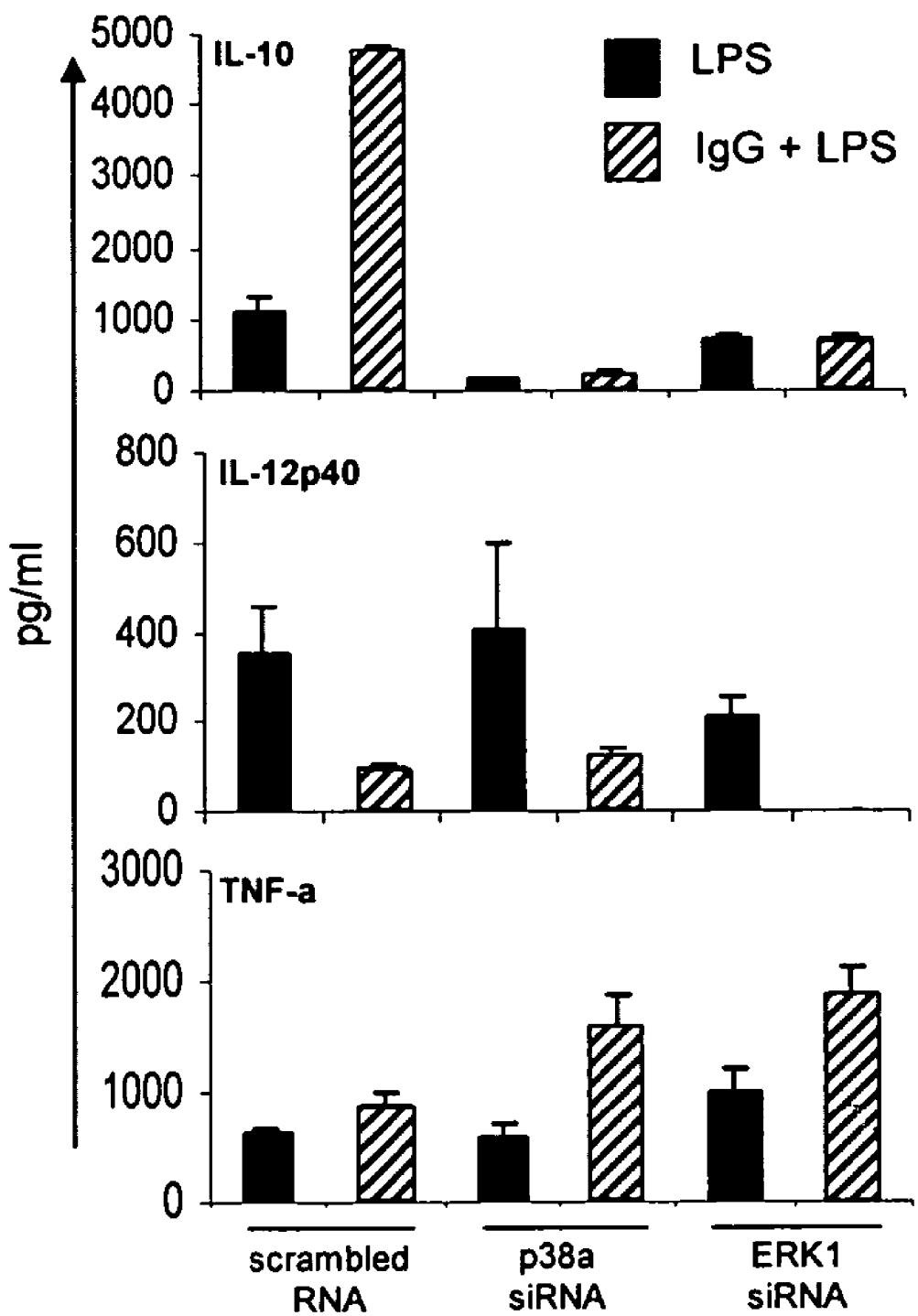
FIG. 3 is a graph of the enzyme-linked immunosorbant assay (ELISA) determination of IL-10, IL-12p40 and TNF alpha in the supernatants of bone marrow derived macrophages (BMMφ) that had been transfected at day 7 with sequence specific siRNA or scrambled sequence dsRNA and cultured for an additional 48 hours in the presence of LPS alone or LPS in combination with IgG. Sequence specific siRNA for p38α or ERK1 (100 nM) or scrambled sequence dsRNA were transfected into day 7 bone marrow-derived macrophages (BMMφ). Cells were cultured for an additional 48 h and then stimulated with LPS (10 ng/ml) alone (solid bars) or LPS+E-IgG (striped bars). Supernatants were harvested after 20 h and cytokines analyzed by ELISA. Data represent the mean level of cytokine+SD of triplicate samples. This figure is representative of 3 individual experiments.

To confirm a specific role for the two MAPKs in IL-10 induction, 100 nM of siRNA specific for p38α or ERK1 were transfected into primary BMMφ48 h before stimulation. Gene silencing was confirmed by real time PCR (data not shown). p38α siRNA almost completely abrogated IL-10 production by macrophages stimulated with either LPS alone or LPS in combination with immune complexes (FIG. 3). ERK1 siRNA had only a modest effect on LPS-induced IL-10 production, but it completely prevented the augmentation of IL-10 production caused by the addition of immune complexes. Thus, p38 inhibition profoundly affects LPS-induced IL-10 production, whereas ERK inhibition primarily affects the augmented IL-10 production resulting from coupling LPS stimulation with FcγR ligation. Therefore, ERK activation is a primary focus for superinduction of IL-10 in response to immune complexes.

Figure 4:
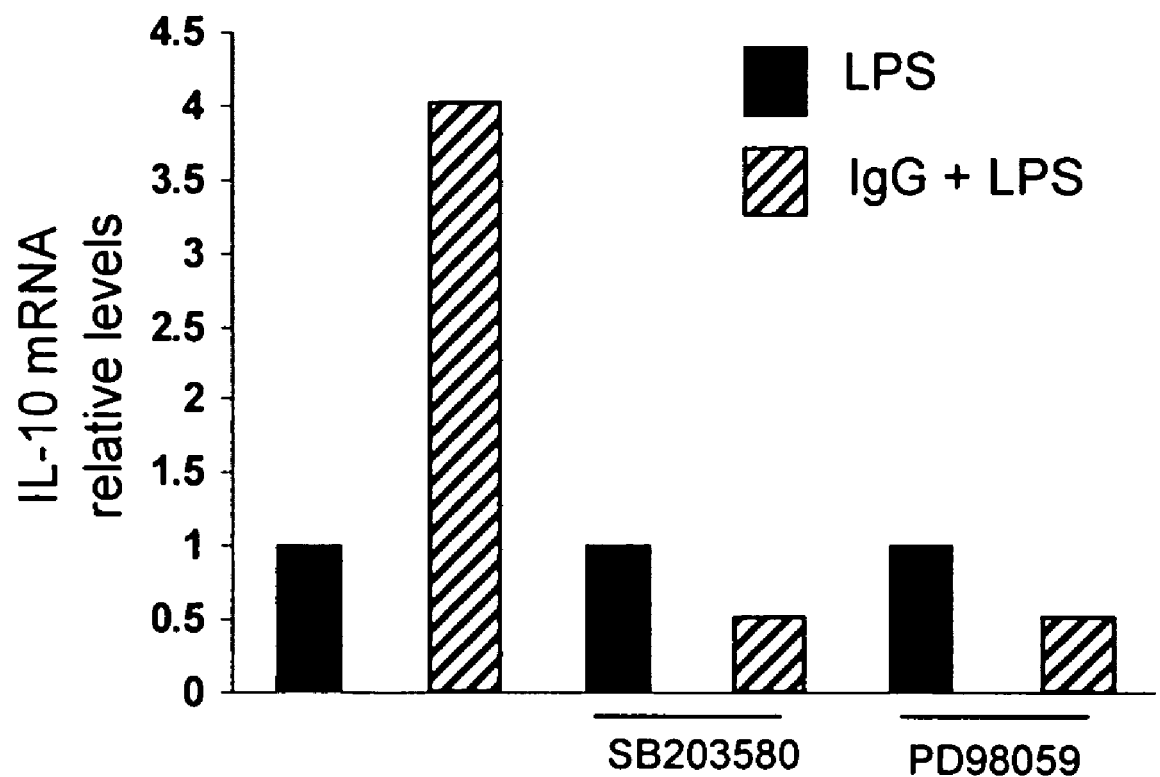
FIG. 4 is a graph showing the Real Time PCR determination of IL-10 mRNA in BMMφ exposed to inhibitors PD98059 and SB203580, in the presence of (LPS) alone or LPS in combination with IgG. BMMφ were pretreated with SB203580 (1 μM), PD98059 (10 μM) or saline for 30 min, and then stimulated with LPS (10 ng/ml) with (striped bars) or without (solid bars) E-IgG for 2 h. Total RNA was reverse transcribed and analyzed by real time PCR. Samples were normalized to a GAPDH control.

To determine the level at which IL-10 was being inhibited, real time PCR analysis was performed to measure IL-10 mRNA in macrophages stimulated with LPS in the presence or absence of immune complexes. As previously reported (Gerber, J. S. and D. M. Mosser. 2001. *J. Immunol.* 166:6861-6868), macrophages stimulated in the presence of immune complexes (FIG. 4, striped bars) had an increased amount of IL-10 mRNA, relative to macrophages stimulated with LPS alone (FIG. 4, solid bars). This induction of IL-10 mRNA was prevented by stimulating these cells in the presence of either ERK or p38 inhibitors (FIG. 4). The JNK inhibitor 1 peptide had no affect on IL10 mRNA levels (data not shown). The increased IL-10 mRNA accumulation that accompanies activation in the presence of immune complexes, was not due to differences in IL-10 mRNA stability (supplemental data).

Figure 5:
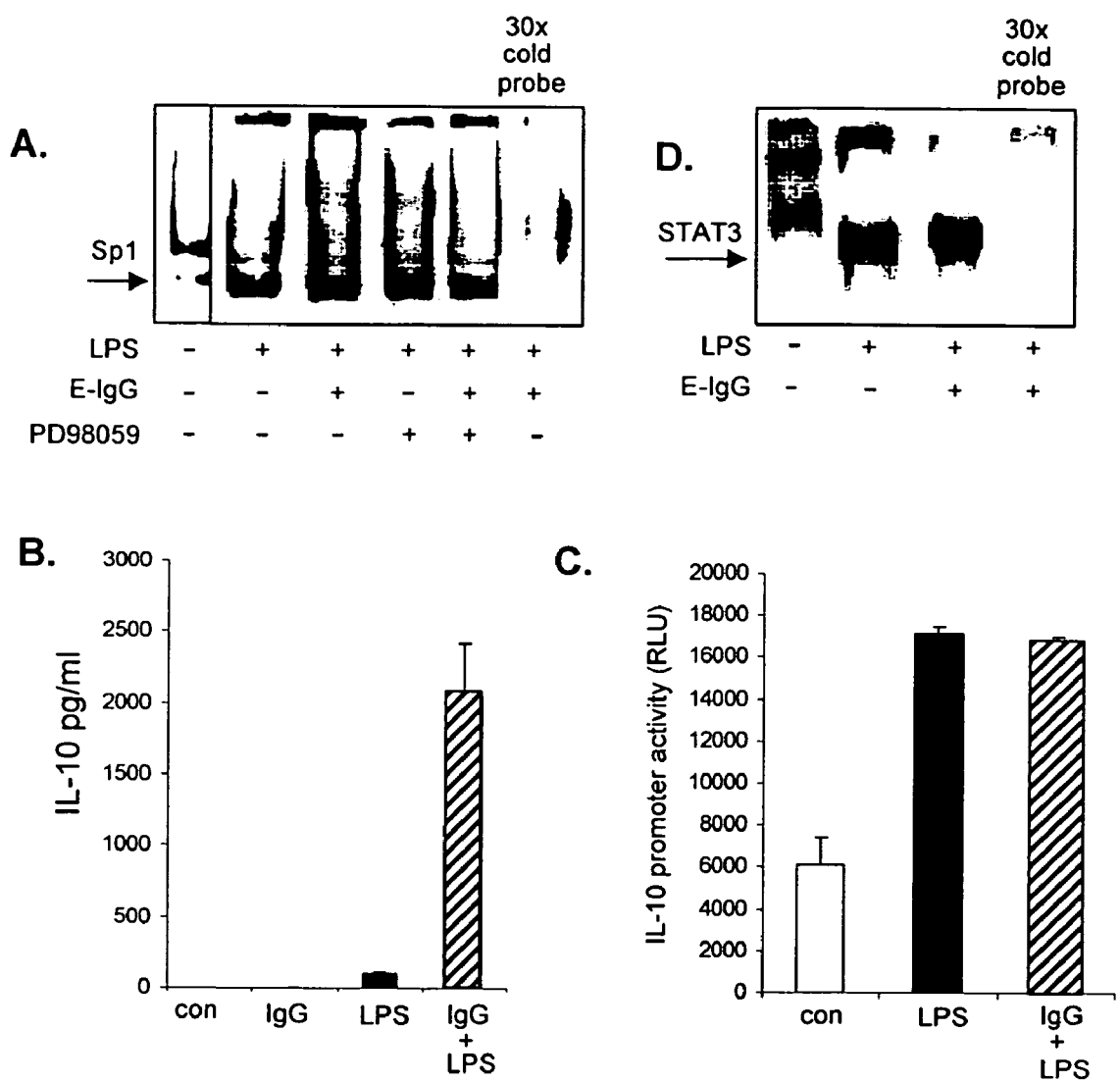
FIG. 5 A-D shows activation of transcription factors in LPS-stimulated BMMφ with or without FcγR ligation. A. Cells were stimulated with LPS (10 ng/ml) or LPS+E-IgG for 30 min and nuclear extracts were analyzed by EMSA using Sp1 (A) or STAT3 (B) specific probes. C. RAW264.7 cells were stimulated with medium (open bar), E-IgG (dotted bar), LPS (solid bar) or LPS+E-IgG (striped bar) and cytokines measured by ELISA after 6 h. Data represents the mean of triplicate samples±SD. D. RAW264.7 cells were transfected with pRL-IL10-luciferase reporter plasmid (5 ug/ml) and 24 h later stimulated with medium (con), 10 ng/ml LPS (solid bar) or E-IgG+LPS (striped bar) for 4 h. Cells were then lysed and luciferase activity measured. This figure is representative of 3 experiments.

Failure of immune complexes to stimulate extrachromosomal IL-10 promoters. To determine whether the addition of immune complexes to stimulated macrophages had any effect on the binding of transcription factors to the IL-10 promoter, EMSA assays were performed, using Sp1 and STAT-3, two transcription factors that have been implicated in IL-10 synthesis (Brightbill, H. D., et al. 2000. *J. Immunol.* 164:1940-1951; Benkhart, E. M., et al. 2000. *J. Immunol.* 165:1612-1617). By EMSA, stimulation of macrophages with LPS caused a significant increase in the binding of both Sp1 (FIG. 5A) and STAT3 (FIG. 5B) to their respective binding motifs in the IL-10 promoter. In both cases, this binding was specific, and was efficiently competed for by a 30-fold excess of cold probe. Coupling macrophage stimulation with immune complexes did not increase the binding of either transcription factor to the IL-10 promoter. Equivalent amounts of Sp1 and STAT3 were bound to DNA following activation in the presence or absence of E-IgG. Furthermore, the inhibition of ERK activation with PD98059 had no effect on Sp1 binding to the IL-10 promoter (FIG. 5A). Thus this data shows that transcription factor activity is not affected by the MAPK pathway.

Additional studies to examine IL-10 transcription were performed on RAW 264.7 macrophage-like cells, transfected with an IL-10 promoter luciferase reporter construct. By ELISA, RAW264 cells behaved similarly to primary macrophages, producing only modest amounts of IL-10 in response to LPS alone, but much higher amounts of IL-10 when stimulation with LPS and immune complexes (FIG. 5C). The production of luciferase driven by an IL-10 promoter, however, did not reflect this superinduction. Unstimulated RAW cells expressed a relatively modest level of luciferase activity, and stimulation of these cells with LPS resulted in a significant increase in luciferase activity (FIG. 5D, solid bars). This activity, however, was not further increased by the stimulation in the presence of immune complexes (FIG. 5D, striped bars). This lack of response to immune complexes is in contrast to our previous observations with IL-12 reporter constructs, which were dramatically reduced upon the addition of immune complexes (Ma, W., et al. 2001. *J. Biol. Chem.* 276:13664-13674). Thus, although immune complexes cause a dramatic increase in IL-10 secretion by macrophages, these increases could not be detected when using assays dependent on extrachromosomal DNA. Neither the EMSA nor the luciferase reporter assays reflected this increase in IL-10 production following the addition of immune complexes.

Figure 6:
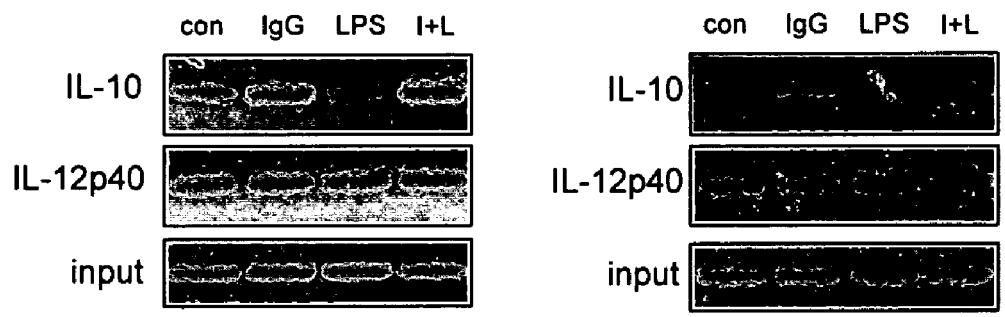
FIG. 6 A-B shows a ChIP analysis of histone H3 modifications at the IL-10 promoter in stimulated BMMφ. BMMφ were stimulated with medium (open bars), LPS (solid bars) or E-IgG+LPS (striped bars) for 15 minutes (A), or the indicated times (B) and ChIP assays were carried out as described in Materials and Methods. Immunoprecipitations utilized antibodies specific to phospho-H3 (left panel) or acetyl-H3 (right panel). A. conventional RT-PCR and B. real time PCR were carried out using IL-10 promoter or IL-12p40 promoter specific primers. For real time PCR, samples were normalized to input DNA controls.
Figure 6:
Figure 6:
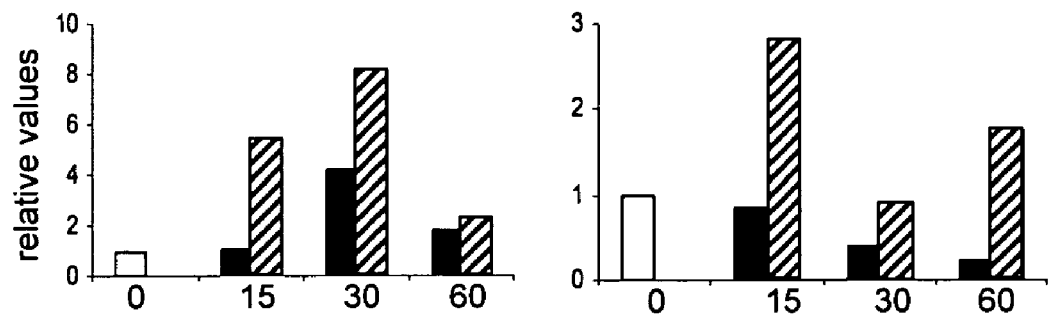

Activation of MAPKs by FcγR results in histone modifications at the IL-10 promoter. To determine the mechanism whereby ERK activation leads to increased IL10 transcription, we examined histone modifications at the IL-10 locus by chromatin immunoprecipitation (ChIP) assays. Histone modifications, such as acetylation and phosphorylation, are thought to be important events in the regulation of gene expression (Anderson, C. F. and D. M. Mosser. 2002. *J. Leukoc. Biol.* 72:101-106), and ERK in particular has been postulated to phosphorylate core histone proteins, including histone H3 (Saccani, S., et al. 2002. *Nat. Immunol.* 3:69-75). ChIP assays were performed on Mφ activated by LPS in the presence or absence of E-IgG. Mφ treated with E-IgG had higher levels of phosphorylated H3 (Ser 10) associated with the IL-10 promoter relative to resting (control) or LPS stimulated Mφ (FIG. 6A). We also performed ChIP assays using an antibody specific to acetylated lysines on histone H3. A similar pattern of increased acetylated H3 associated with the IL-10 promoter was observed following FcγR ligation, although the amount of acetylation appears to be more modest (FIG. 6A). Both phosphorylation and acetylation events were time dependent events. Phosphorylation occurred rapidly and peaked at 30 minutes, whereas the low level of histone H3 acetylation persisted for 1-2 hours post-stimulation (FIG. 6B). For these assays, the IL-12 (p40) promoter was used as a control. Histones associated with the IL-12 promoter were neither phosphorylated nor acetylated in response to immune complexes (FIG. 6A). Therefore FcγR signaling results in histone modifications which are specific to the IL-10 promoter.

To correlate histone phosphorylation with ERK activation, similar studies were performed on macrophages that were stimulated with a soluble immune complex, in the presence or absence of PD98059 to prevent ERK activation. Similar to the previous figure, which used E-IgG as the immune complex, the addition of IgG-OVA, caused a dramatic increase in histone phosphorylation, and this increase was completely abrogated by inhibiting ERK activation (FIG. 7A). ERK inhibition reduced the amount of histone phosphorylation at this locus to background levels (FIG. 7B). The inhibition of p38 with SB203580 had a more modest effect on histone H3 phosphorylation, decreasing it substantially, but not reducing it to background levels (FIG. 7B).

To determine the fine specificity of nucleosome modifications, the twelve successive nucleosomes located 5' of the IL-10 transcriptional start site were individually analyzed for modifications following stimulation. Data from three of these sites are shown in FIGS. 12A-C. The two nucleosomes comprising the Sp1 (FIG. 12A) and the STAT3 (FIG. 12B) sites underwent rapid and extensive increases in Histone H3 phosphorylation following the addition of immune complexes. This phosphorylation was transient and reduced to basline levels within 1 hour post-stimulation, a time at which acetylation peaks (FIGS. 12A and 12B). A similar analysis was performed on a control nucleosome located ~1500 BP away from the transcriptional start site. There was little detectable increase in either phosphorylation or acetylation at this site (FIG. 12C). The extent of histone modifications at this site was comparable to that which occurred at the IL-12 promoter (see FIGS. 6 and 7).

Figure 8:
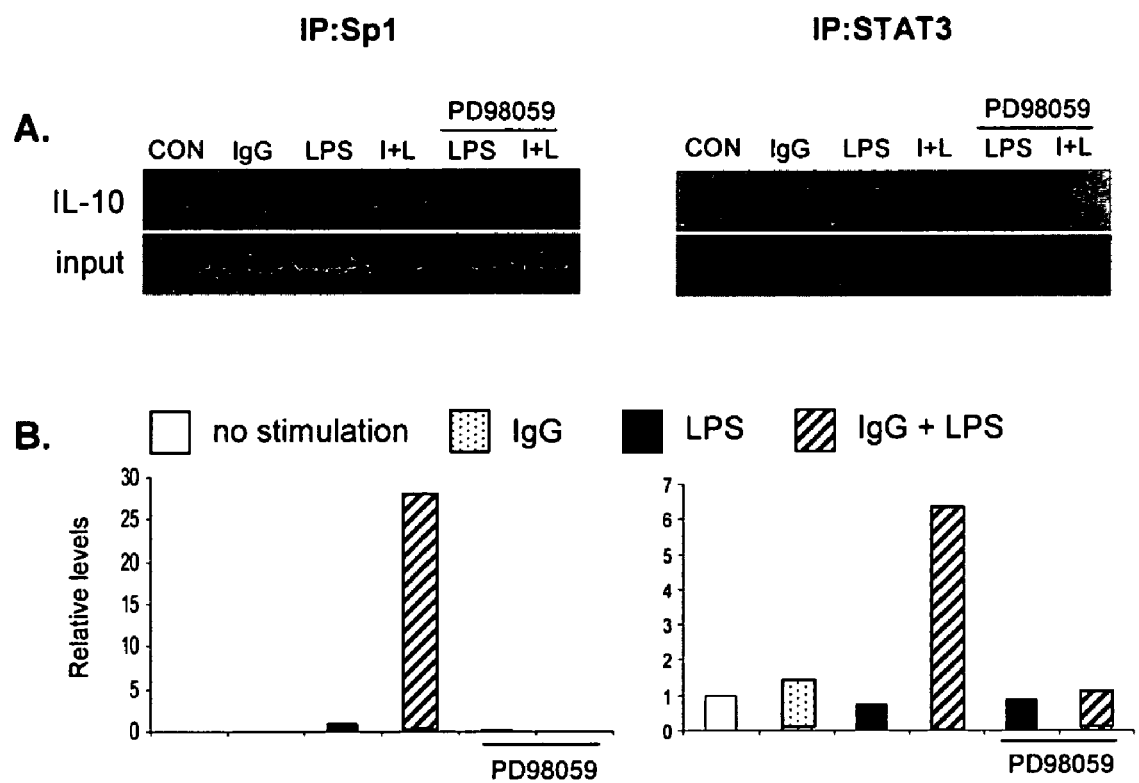
FIG. 8 A-B shows a ChIP analysis of Sp1 and STAT3 binding at the IL-10 promoter in stimulated BMMφ. BMMφ were stimulated with medium (open bar), E-IgG (dotted bar), LPS (solid bar), or LPS+E-IgG (striped bar) for 40 min. Some cells were pretreated with PD98059 (10 μM). Immunoprecipitations were carried out using either Sp1 or STAT3 specific Abs. A. Conventional RT-PCR was carried out using primers which amplify the putative Sp1 or STAT3 binding sites of the IL-10 promoter respectively. B. Real time PCR analysis of samples obtained in A. Samples were normalized to input DNA controls.

Transcription factor binding to the IL-10 promoter in situ. Having failed to detect increased transcription factor binding to an extrachromosomal IL-10 promoter element by EMSA (FIG. 5), we next performed ChIP assays to examine the binding of Sp1 and STAT3 to the IL-10 promoter in situ within live cells (FIG. 8A). Control (unstimulated) cells exhibited virtually no binding of either Sp1 or STAT3 to the IL-10 promoter. Similarly, the addition of immune complexes to resting cells, a condition which does not induce IL-10 production from macrophages (Gerber, J. S. and D. M. Mosser, 2001 *J. Immunol.* 166:6861-6868), also failed to result in transcription factor binding to the IL-10 promoter (FIG. 8A). Stimulation of cells with LPS alone, a condition that induces low levels of IL-10 production, caused a modest increase in Sp1 binding to the IL-10 promoter, but no detectible STAT3 binding. However, LPS plus immune complexes induced the efficient binding of both Sp1 and STAT3 to the IL-10 promoter. Thus, unlike the reporter assays described above, which utilized extrachromosomal IL-10 promoters, the ChIP assays for Sp1 and STAT3 binding to the IL-10 promoter were accurate reflections of IL-10 transcription. Both transcription factors bound to the IL-10 promoter in situ under conditions of IL-10 superinduction. Furthermore, inhibiting ERK activation with PD98059, a condition which prevented IL10 induction, reversed transcription factor binding to the IL-10 promoter (FIG. 8B).

To correlate transcription factor binding with DNA accessibility, chromosomal DNA in resting and activated cells was digested with DNAse I. In resting cells, the IL-10 promoter was relatively resistant to DNase I treatment (FIGS. 13A and 13B). In cells exposed to immune complexes, either alone or in combination with LPS, however, there was a rapid increase in the sensitivity to DNase I treatment. This sensitivity was induced within 30 minutes of stimulation, and it persisted for the entire 3 hour observation period. Thus, immune complexes alone are sufficient to activate ERK, to modify chromatin, and to make the IL-10 locus more accessible. These immune complexes, however, are not sufficient to induce IL-10 expression. The induction of IL-10 requires a second signal, which is provided by stimulating the cells to activate the transcription factors, which bind to the accessible IL-10 promoter.

Discussion

We have previously shown that activation of macrophages in the presence of immune complexes increases their production of IL-10 and reduces IL-12 production (Mosser, D. M. 2003. *J. Leukoc. Biol.* 73:209-212). This gives rise to a population of macrophages with potent anti-inflammatory properties. We have termed these cells Type II activated macrophages or MφII. We have previously shown that this response to immune complexes occurs in macrophages taken from a variety of different species, including mice and man, from various anatomical locations, including the peritoneum, lung, and blood (Anderson, C. F. and D. M. Mosser. 2002. *J. Leukoc. Biol.* 72:101-106). It also occurs following many different types of macrophage stimulation, including LPS, LTA, and CD40L (Gerber, J. S. and D. M. Mosser. 2001. *J. Immunol.* 166:6861-6868), and in the presence of several different soluble or particulate immune complexes (Anderson, C. F. and D. M. Mosser. 2002. *J. Immunol.* 168:3697-3701; Mosser, D. M. 2003. *J. Leukoc. Biol.* 73:209-212). Thus, we feel that this response to FcγR ligation is a universal response that is a general property of most, if not all, macrophages. In the present work we sought to determine the mechanism whereby IL-10 was induced in response to immune complexes.

Immune complexes alone were not sufficient to induce IL-10. Rather cytokine production required both a stimulation (LPS) and the addition of immune complexes. Only the combination of these two stimuli resulted in high levels of IL-10 production. Therefore, we examined signal transduction in macrophages, following the addition of each stimulus alone or in combination. LPS alone signals through TLRs to induce NF-κB translocation and moderate levels of MAPK activation, as previously described (Akira, S., et al. 2001. *Nat. Immunol.* 2:675-680). While these signals were sufficient to maximally activate extrachromosomal IL-10 constructs, LPS alone induced only modest levels of IL-10 secretion by macrophages. This low level of IL-10 could be completely blocked by inhibiting p38 (see FIG. 3). The coupling of LPS with immune complexes, however, resulted in a substantial increase in IL-10 production. Thus, signals generated via FcγRs converge with those generated by TLRs to induce high levels of IL-10. We show that FcγR ligation caused a rapid increase in ERK activation. This activation was required for IL-10 production, but not sufficient. ERK activation had to be coupled with an inflammatory stimulus in order to induce IL-10. The inflammatory stimuli activate the myriad transcription factors that drive cytokine and co-stimulatory molecule expression. In the absence of ERK activation, however, these activated transcription factors fail to effectively induce IL-10 production. In the present work, we show that activation of ERK makes the IL-10 promoter accessible to these transcription factors, resulting in the production of high levels of IL-10.

Several groups have correlated cytokine production with MAPK activation (Saccani, S., et al. 2002. *Nat. Immunol.* 3:69-75) and some investigators have recently suggested that differential activation of the MAPKs may lead to differences in cytokine production (Mathur, R. K., et al. 2004. *Nat. Med.* 10:540-544). We confirm the observation of Mathur and colleagues that p38 activation is linked to inflammatory cytokine production, and that ERK activation can lead to the production of IL-10. In the present work we show that the mechanism of IL-10 induction is the activation of ERK, which leads to chromatin modifications at the IL-10 locus, to make the promoter more accessible to transcription factors that bind to it.

It has been well-established that covalent modifications to chromatin, including acetylation, phosphorylation, methylation and even ubiquitination can influence gene expression (Turner, B. M. 2002. *Cell* 111:285-291). In fact, some have suggested that the specific combination of histone modifications represents a code which can determine gene expression (Strahl, B. D. and C. D. Allis. 2000. *Nature* 403:41-45). In the case of differentiated lymphocytes, some of these modifications can lead to long term heritable changes in gene expression, which can define the very phenotype of the cell (Murphy, K. M. and S. L. Reiner. 2002. *Nat. Rev. Immunol.* 2:933-944). Epigenetic changes in gene expression have been associated with T cell deviation along the Th1 or Th2 pathway. In fact, a recent study has demonstrated that IL-10 chromatin becomes altered as T cells commit to the Th2 lineage (Im, S. H., et al. 2004. *J. Biol. Chem.* 279:46818-46825). The alterations described in the present work also depend on chromatin alterations, and appear to utilize some of the same types of histone modifications that lead replicating cells to undergo these epigenetic changes in gene expression. In the present situation, however, these changes occur quite rapidly, and their effect is transient. Alterations to chromatin are observed within the first fifteen minutes of stimulation, and they can be reversed as quickly as an hour later (see FIG. 8). Furthermore, in end-stage cells such as macrophages, these need not be heritable alterations that can be passed on to daughter cells, and therefore their effect is transient and reversible.

Although histone phosphorylation was originally associated with chromatin condensation and gene silencing during cell division (Cheung, P., et al. 2000. *Cell* 103:263-271), several studies have correlated histone modifications and specifically phosphorylation of the serine 10 residue on histone H3 with transcriptional activation (Saccani, S., et al. 2002.

*Nat. Immunol.* 3:69-75; Nowak, S. J. and V. G. Corces. 2004. *Trends Genet.* 20:214-220). In fact, a human genetic disease, called Coffin-Lowry Syndrome, is characterized by impaired transcription of c-fos and defective histone H3 phosphorylation (Trivier, E., et al. 1996. *Nature* 384:567-570). The acetylation of histones has also been linked to transcriptional activation (Agalioti, T., et al. 2002. *Cell* 111:381-392), and frequently histone acetylation occurs in association with histone phosphorylation. In yeast, phosphorylation often precedes, and can be a prerequisite for, histone acetylation (Lo, W. S., et al. 2001. *Science* 293:1142-1146), whereas in Drospohila these two modifications may be independently regulated (Labrador, M. and V. G. Corces. 2003. *Genes Dev.* 17:43-48). Although the dramatic increase in early histone H3 phosphorylation following exposure of macrophages to immune complexes requires ERK activation, it is unlikely that ERK directly modifies chromatin. Rather, several histone H3 kinases have been identified which represent candidates for the observed phosphorylation events. Work is underway to identify the IL-10-associated histone kinase. Importantly, the alterations to chromatin that we observe appear to be restricted to the IL-10 gene, in that no such modifications are observed at the IL-12 gene. Further analyses to determine the mechanism of this modification are discussed in Example 5.

The increase in IL-10 production following activation in the presence of immune complexes makes these macrophages potent anti-inflammatory cells (Gerber, J. S. and D. M. Mosser. 2001. *J. Immunol.* 166:6861-6868). In the present work we show that stimulation of cells with LPS alone leads to modest levels of ERK activation, modest binding of Sp1 to the IL-10 promoter in situ, and only low levels of IL-10 gene expression. Coupling stimulation with FcγR ligation, however, leads to increased ERK activation, histone H3 modifications at the IL-10 locus, and dramatic increases in Sp1 and STAT3 binding to the IL-10 promoter. We believe that these modifications are required for the high levels of IL-10 that are produced by macrophages activated in the presence of immune complexes, and suggest that manipulating MAPK activation in macrophages can change the phenotype of the activated macrophage.

Example 2

ERK Activation and IL-10 Induction by CSF-1

Macrophages were stimulated with LPS alone or LPS plus CSF-1 or CSF-1 plus 8Br-cAMP using procedures similar to those described in Example 1. CSF-1 was used at 100 ng/ml and added simultaneously with the LPS. 8Br-cAMP was added 30 minutes prior to stimulation. IL-10 was measured 20 hrs later by ELISA (FIG. 9A).

Macrophages were stimulated with LPS alone or LPS plus CSF-1 or CSF-1 plus 8Br-cAMP using procedures similar to those described in Example 1. Cells were lysed at various indicated times and ERK activation was measured by Western Blot using antibodies to phosphorylated ERK (FIG. 9B).

CSF-1 is an example of a compound that activated ERK but not p38 and therefore, CSF-1, does not induce IL-10 on its own. However, when macrophages are treated with CSF-1 and then exposed to bacterial cell walls (e.g. stimulated with LPS) they induce more IL-10 as shown in FIGS. 9A and 9B.

Example 3

IL-10 Induction by PMA

PMA activates protein kinase C and MAP kinase. Macrophages were stimulated with LPS in the presence of absence of PMA using procedures similar to those described in Example 1. IL-10 production was measured by ELISA 20 hour later. The data is shown in FIG. 10A.

Macrophages were stimulated with LPS in the presence or absence of PMA using procedures similar to those described in Example 1. ERK activation was analyzed at the indicated times by Western Blot, using antibodies to phosphorylated ERK. The data is shown in FIG. 10B.

Figure 10A:
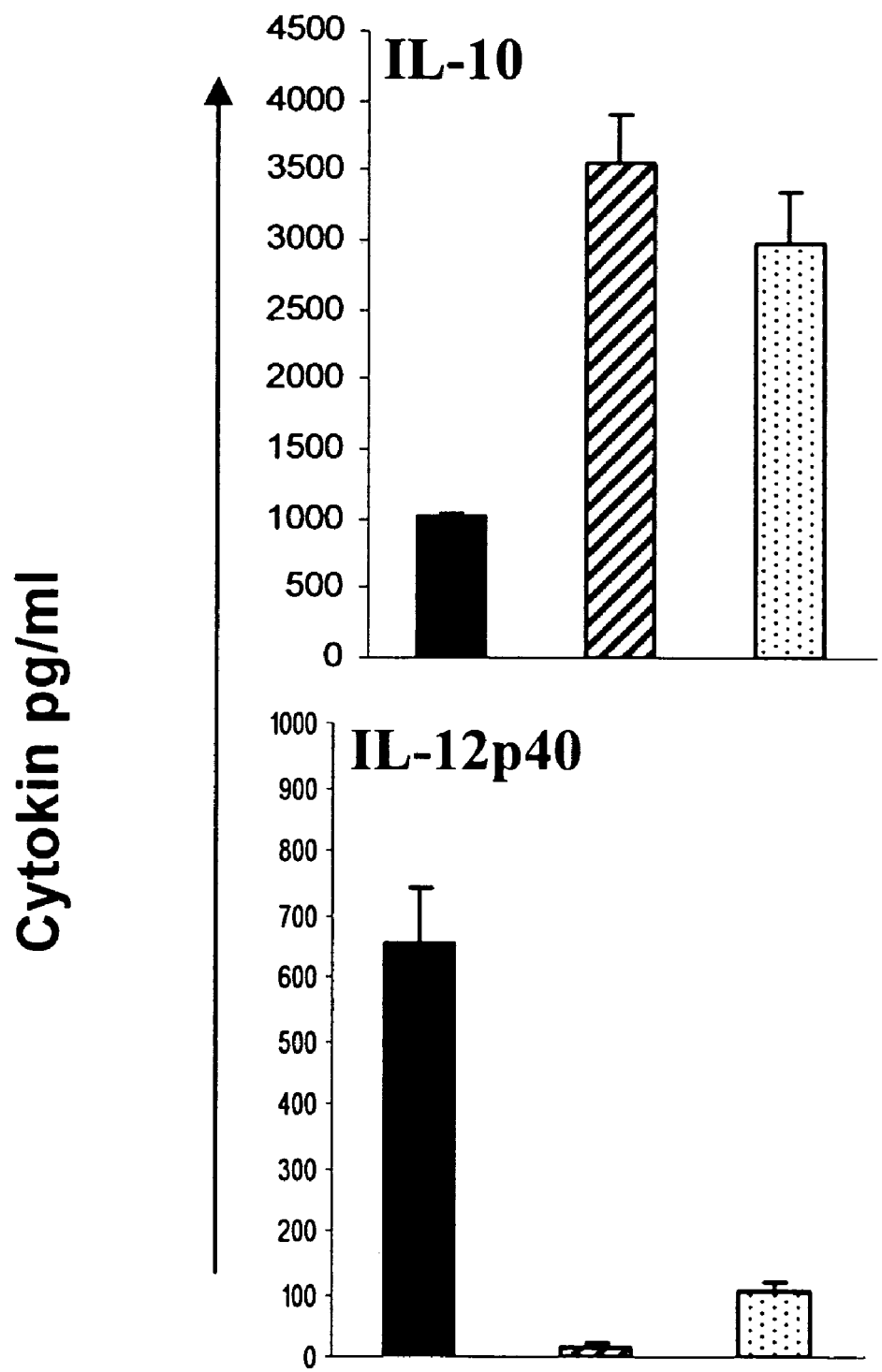
FIG. 10A is a graph showing IL-10 induction by phorbol 12-myristate 13-acetate (PMA). Macrophages were stimulated with LPS in the presence or absence of PMA. IL-10 production was measured by ELISA 20 hrs later.
Figure 10B:
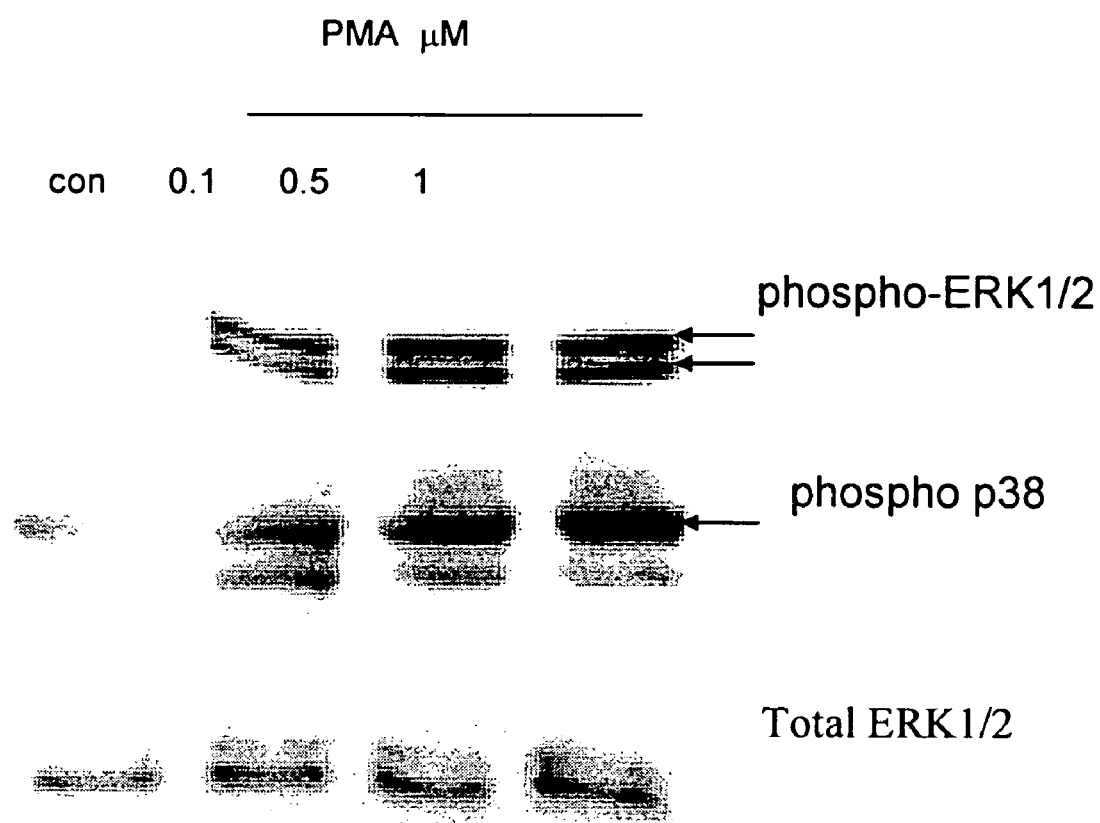
FIG. 10B is a Western Blot showing IL-10 induction by PMA. Macrophages were stimulated with LPS in the presence or absence of PMA. ERK activation was analyzed at the indicated times by Western blot, using antibodies to phosphorylated ERK.

As shown in FIGS. 10A and 10B PMA activated ERK and induced IL-10. This data indicates that activation of ERK and p38 by PMA mimics FcγR-ligation in BMMφ. The implications are that any exogenous activator of ERK will predispose the macrophage to produce IL-10 in response to inflammation.

Example 4

High Throughput Screen for ERK Activators

To screen for ERK activators, Applicants take advantage of the fact that activated ERK can phosphorylate a transcription factor, called Elk. Phosphorylated Elk drives the transcription of genes that have an Elk binding site in their promoter. Thus Applicants screen for Elk-mediated gene transcription to detect ERK activators. In the actual screen, the gene that is transcribed is luciferase, because it is easy to detect. Rather than place an Elk binding domain upstream of luciferase, a yeast transcription factor binding domain is used instead. Then, instead of using intact Elk, Applicants use a construct encoding a fusion protein, consisting of the transcriptional activation domain of Elk and a yeast transcription factor DNA binding domain. Thus, ERK activation leads to the phosphorylation of the Elk portion of the fusion protein, which binds to the DNA upstream of the luciferase reporter gene. Activation of luciferase in reporter cells means that ERK has been activated.

Figure 14:
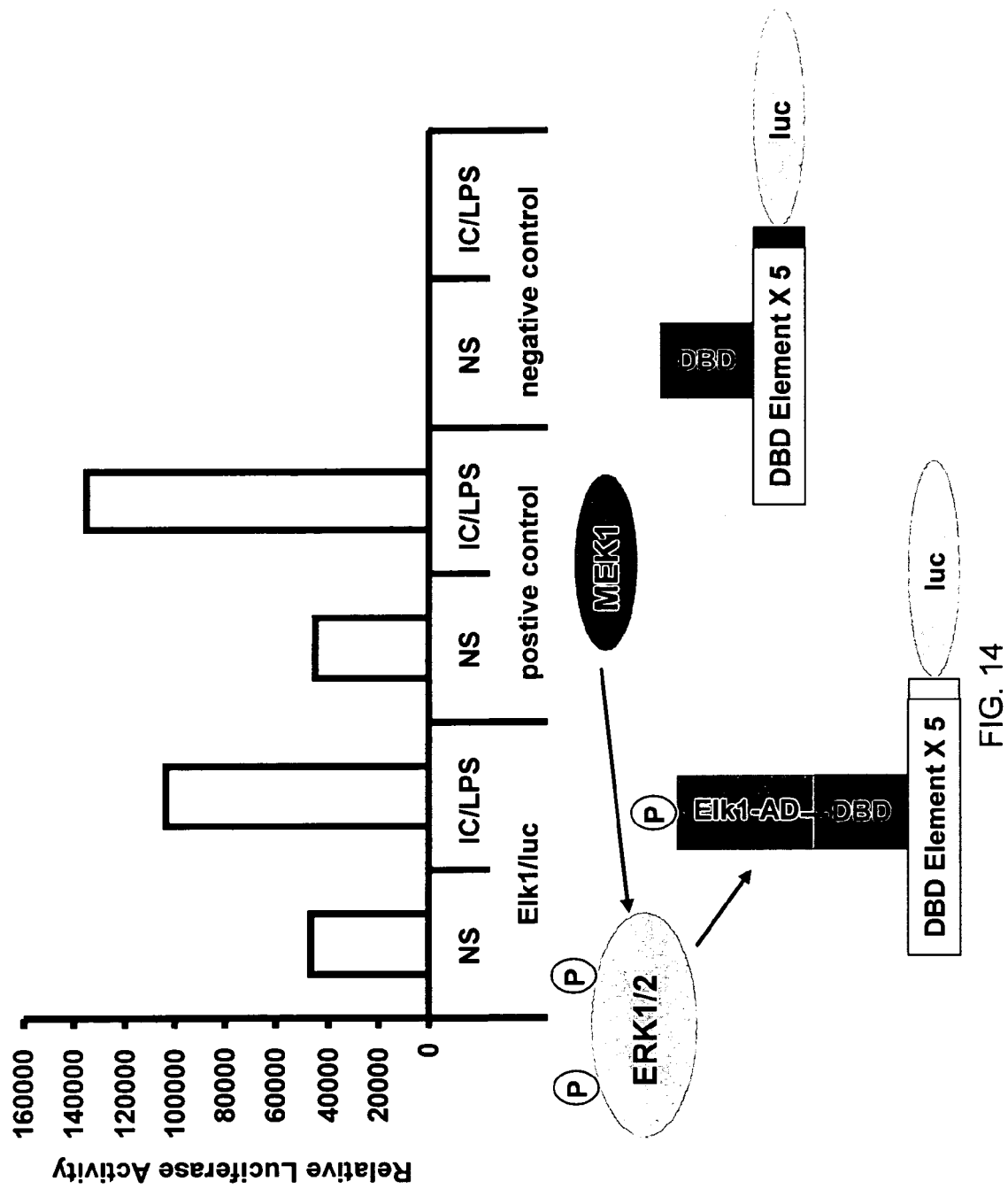
FIG. 14 is a schematic of an assay useful in the invention showing a schematic of the constructs and a graph of the relative luciferase activity of the construct compound versus the controls.

The specifics of the assay are as follows: The RAW 264.7 macrophage cell line was obtained from the American Type Culture Collection (Rockville, Md.) and cultured in DMEM/RPMI-1640 (50/50) medium supplemented with 10% FCS. The PathDetect®Elk1 trans-Reporting System was purchased from Stratagene (La Jolla, Calif.). This system contains the pFR-luciferase reporter plasmid, and the pFA2-Elk1 fusion trans-activator plasmid. This system also contains negative and positive control plasmids. A stably-transfected cell line was established by electrophoration of pFR-luciferase, and pFA2-Elk1 into RAW 264.7 cells. Cells that were stably transfected were selected by resistance to G418 (1 mg/ml) (Invitrogen, Rockville, Md.). When these cells are exposed to 10 ng/ml LPS plus immune complexes, they increase luciferase activity (FIG. 14).

For proof of concept, negative and positive control transfected cells are also generated. Negative control cells are transfected with the pFR-luciferase reporter plasmid and a plasmid encoding only the DNA binding domain of the fusion protein without the Elk transcriptional activation domain. A positive control is transfected with the two plasmids described above, and an additional plasmid that encodes the Map Kinase Kinase, called MEK1. MEK is the kinase that activates ERK.

In the screen, compounds that induce luciferase activity, will be selected and then analyzed for IL-10 inducing activity by ELISA. An example of the ELISA measuring IL-10 production is discussed in Example 3.

Example 5

Histone Phosphorylation at the IL-10 Promoter

To gain insight into the molecular mechanism(s) whereby macrophages produce large amounts of IL-10, we analyzed IL-10 gene expression and temporally correlated it with modifications to chromatin associated with the IL-10 promoter. In resting cells, which make essentially no cytokines, the IL-10 promoter is associated with histones containing little or no detectable modifications. Macrophages stimulated in the presence of immune complexes begin to produce high levels of IL-10 pre-mRNA transcripts within minutes of stimulation. Coincident with this transcription was a rapid and dynamic phosphorylation of histone H3 at specific sites in the IL-10 promoter. The phosphorylation of histones was closely followed by the binding of transcription factors to the IL-10 promoter. Blocking the activation of ERK prevented histone phosphorylation and transcription factor binding to the IL-10 promoter. In contrast to histone phosphorylation, the peak of histone acetylation at this promoter did not occur until after transcription had peaked. Furthermore, inhibiting HDAC activation did not increase IL-10 production, suggesting that phosphorylation but not acetylation was the proximal event responsible for IL-10 transcription. Our findings reveal a rapid and well-orchestrated series of events in which ERK activation causes a rapid and transient phosphorylation of histone H3 at specific regions of the IL-10 promoter, resulting in a transient exposure of the IL-10 promoter to the transcription factors that bind there. This exposure is essential for the efficient induction of IL-10 gene expression in macrophages. To our knowledge, this represents a unique way in which the expression of a cytokine gene is regulated.

Reagents

The MEK/ERK inhibitor, PD98059, and the histone deacetylase (HDAC) inhibitor, Trichostatin A (TSA), were obtained from Calbiochem (EMD Biosciences, Inc., San Diego, Calif.). Ultra pure LPS from *Escherichia coli* K12 strain was purchased from InvivoGen (San Diego, Calif.). Anti-phosphorylated histone H3 (Ser10) antibody, anti-acetylated histone H3 (Lys14), and anti-Sp1 antibody were obtained from Upstate USA, Inc. (Charlottesville, Va.). TRIzol® reagent was purchased from Invitrogen (Carlsbad, Calif.). RNase-free DNase I and micrococcal nuclease (MNase) were obtained from Roche Diagnostics (Indianapolis, Ind.).

Mice

Six- to 8-wk-old Balb/c mice were purchased from Taconic Farms (Germandown, N.Y.). All mice were maintained in HEPA-filtered Thoren units (Thoren Caging Systems, Hazleton, Pa.) at the University of Maryland (College Park, Md.). Mice were used at 6-10 weeks of age as a source of BMMφ. All procedures were reviewed and approved by the University of Maryland Institutional Animal Care and Use Committee.

Bone Marrow Derived Macrophages (BMMφ), and Immune Complex (IC)

BMMφ were prepared as previously described (Sutterwala, F. S., et al. 1998. *J. Exp. Med.* 188:217). Briefly, bone marrow was flushed from the femurs and tibiae of mice, and cells were plated in Petri dishes in complete medium, which consists of DMEM/F12 supplemented with 10% FBS, penicillin/streptomycin, glutamine, and 20% L-cell conditioned medium (LCM). On day 2 and 5, cells were fed with complete medium. On day 7, cells were removed from Petri dishes and cultured on tissue culture dishes in complete medium without LCM. On the next day, cells were subject to experimentation.

Rabbit polyclonal IgG to chicken egg albumin (anti-OVA IgG) was supplied by Cappel (MP Biomedicals, Inc., Aurora, Ohio). After the lyophilized powder was reconstituted, the contaminating endotoxin was removed by using EndoClean™ from BioVitage (San Diego, Calif.). Chicken egg albumin (OVA) was purchased from Worthington Biochemical Corporation (Lakewood, N.J.) and polymyxin B-agarose (Sigma-Aldrich, St. Louis, Mo.) was used to remove LPS. Immune complex (IC) consisting of IgG-OVA were prepared by mixing 181 μl of RPMI-1640 with 14 μl of chicken OVA (1 mg/mL) and 117 μl of anti-OVA IgG (4 mg/mL) for 30 minutes on a rotary platform at room temperature, as described (Anderson, C. F., and D. M. Mosser. 2002. *J. Immunol.* 168:3697).

Quantitative Real-Time PCR (QRT-PCR)

QRT-PCR was performed on an ABI Prism 7700 Sequence Detection System using SYBR Green® PCR reagents purchased from Bio-Rad Laboratories (Hercules, Calif.). Melting curve analyses were performed after PCR amplification to ensure that a single product with the expected melting curve characteristics was obtained, as described (Lucas, M., X. Zhang, et al. 2005. *J. Immunol.* 175:469).

Cytokine Measurement

Cytokines were measured by sandwich ELISA using Ab pairs provided by BD PharMingen (San Diego, Calif.) (IL-12p70, 9A5 and C17.8; IL-10, JES-2A5 and JES-16E3) according to the manufacture's instructions.

RNA Isolation and Real Time PCR (RT-PCR)

BMMφ ($3-5 \times 10^6$ cells per reaction) were subjected to RNA extraction using TRIzol® reagent. The contaminating DNA was then removed by RNase-free DNase I treatment. ThermoScript™ RT-PCR system (Invitrogen) was used to generate cDNA from RNA by using random hexamers or oligo(dT)$_{20}$. QRT-PCR was employed to measure both mature and pre-mature IL-10 mRNA levels. Pre-mature IL-10 mRNA was analyzed by using random hexamers-generated cDNA and the primer pairs: sense 5'-CATTCCAGTAAGTCACAC-CCA-3' (SEQ ID NO: 19) (intronic primer) and anti-sense 5'-TCTCACCCAGGGAATTCAAA-3' (SEQ ID NO: 20), and GAPDH primer pairs: 5'-TGTTCCTACCCCCAAT-GTGT-3' (SEQ ID NO: 21) and anti-sense 5'-TCCCAAGT-CACTGTCACACC-3' (SEQ ID NO: 22) (intronic primer). Mature IL-10 mRNA was amplified by using oligo(dT)$_{20}$-generated cDNA and the primer pairs: sense 5'-AAGGAC-CAGCTGGACAACAT-3' (SEQ ID NO: 23) and anti-sense 5'-TCTCACCCAGGGAATTCAAA-3' SEQ ID NO: 24), and GAPDH primer pairs: sense 5'-TGTTCCTACCCCCAAT-GTGT-3' (SEQ ID NO: 25) and anti-sense 5'-GGTCCT-CAGTGTAGCCCAAG-3' (SEQ ID NO: 26).

Chromatin Immunoprecipitation (ChIP) Assay

Figure 15:
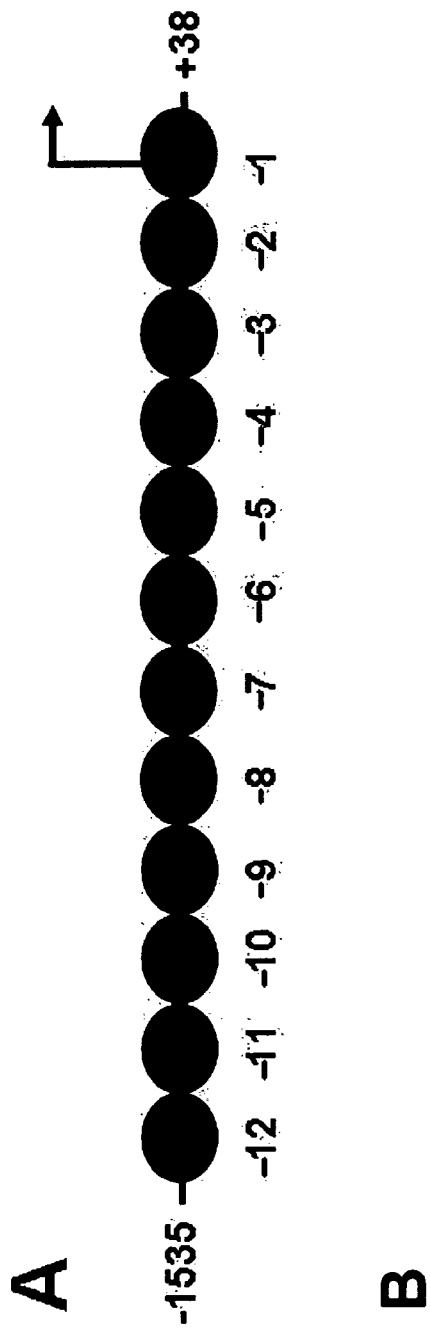
FIG. 15 (A) Schematic illustration representing the nucleosomes along the promoter region of the IL-10 gene and the primer pairs used to amplify each segment of the IL-10 promoter. (B) The primers used to amplify specific regions of the IL-10 promoter are listed, and correspond numerically (i.e. nucleosome at −1 being amplified by primer probe pair 1).

ChIP assays were performed following ultrasonic shearing conditions that result in relatively uniform DNA fragment size of approximately 300 bp. The remaining procedures were carried out as previously described (Lucas, M., X. Zhang, et al. 2005. *J. Immunol.* 175:469). The primers used to amplify specific regions of the IL-b promoter are listed in the table of FIG. 15 (SEQ ID NOS 27-50). TNF-cL primers used for QRT-PCR were: 5'-CCACATGAGATCATG-GTTTTCTC-3' (SEQ ID NO: 51) and 5'-CTGGCTAGTC-CCTTGCTGTC-3' (SEQ ID NO: 52). IL-12p40 primers used for QRT-PCR were: 5'-TTTCGACGTCTATATTCCCTCTG- 3' (SEQ ID NO: 53) and 5'-AGCTGCCTGGTCTGATGTG-3'. IL-12p35 primers used for QRT-PCR were: 5'-CGACG-CACTTGTCCTTGAGAT-3' (SEQ ID NO: 54) and 5'-ACTGAGAGGAGCTGCTGGAT-3' (SEQ ID NO: 55). TdT primers used for QRT-PCR were: 5'-ACCAAGACTGA-CAACCCACGTT-3'(SEQ ID NO: 56) and 5'-GTGGCAGT-CAGAGGCATCTTT-3' (SEQ ID NO: 57).

MNase and DNase I Accessibility Assay

MNase accessibility assay was performed on cells grown in 100-mm tissue culture dishes that were stimulated with LPS/IC. At different time intervals, formaldehyde was added for 15 min at room temperature at a final concentration of 1%, followed by glycine (0.125 M) to neutralize formaldehyde. Cells were washed and lysed in 4 ml of ice-cold Nuclei EZ lysis buffer (Sigma-Aldrich), centrifuged at 500 g for 4 min, and the nuclei were resuspended with an additional 4 ml of ice-cold Nuclei EZ lysis buffer. Washed nuclei were pooled and resuspended in MNase digestion buffer (10 mM Tris-HCl of pH 7.4, 15 mM NaCl, 60 mM KCl, 0.15 mM spermine and 0.5 mM spermidine). After centrifugation at 120 g for 10 min at 4° C., the nuclei were resuspended in MNase digestion buffer containing 1 mM $CaCl_2$. MNase was then added and incubated at room temperature for 5 minutes. The reaction was terminated by adding MNase stop buffer (100 mM EDTA and 10 mM EGTA in 10 mM Tris-HCl of pH 7.4). Proteinase K (100 μg) and RNase A (10 μg) were then added and incubated at 37° C. overnight. DNA was purified with phenol/chloroform extraction and ethanol precipitation. The purified DNA fragments were subjected to QRT-PCR analysis. DNase I accessibility was determined as previously described (Lucas, M., X. Zhang, et al. 2005. J. Immunol. 175:469).

Data Analysis

The relative differences among samples were determined using the $\Delta\Delta C_T$ methods as described in the Applied Biosystems protocol. A $\Delta C_T$ value was determined for each sample using the $C_T$ value from input DNA to normalize ChIP assay results. The $C_T$ value for GAPDH was used to normalize loading in the reverse transcriptase-PCRs. For the MNase or DNase I accessibility assays, $\Delta C_T$ values were determined by subtracting the $C_T$ value from each MNase or DNase I concentration from the zero enzyme control $C_T$ value. A $\Delta\Delta C_T$ value was then obtained by subtracting control $\Delta C_T$ values from the corresponding experimental $\Delta C_T$. The $\Delta\Delta C_T$ values were converted to fold difference compared with the control by raising 2 to the $\Delta\Delta C_T$ power. Student's t test was used for statistical analysis. Values of $p<0.05$ were considered to be statistically significant.

RESULTS

Phosphorylation at Ser10 of Histone H3 across the IL-10 Promoter Region

We previously demonstrated that the stimulation of macrophages with TLR agonists (LPS) combined with immune complexes (IC) resulted in the production of large amounts of IL-10 (Sutterwala, F. S., et al. 1998. J. Exp. Med. 188:217). This superinduction of IL-10 was due, in part, to the activation of the MAP kinase pathway (Lucas, M., X. Zhang, et al. 2005. J. Immunol. 175:469). In the present work we quantitatively and spatio-temporally analyzed changes in histone H3 phosphorylation across the promoter region of the IL-10 gene following stimulation. We generated chromatin fragments with an average size of 300 bp (FIG. 1), which, in combination with QRT-PCR, allowed a high resolution profiling of histone modifications across the first 1600 bases of the IL-10 promoter.

Figure 16:
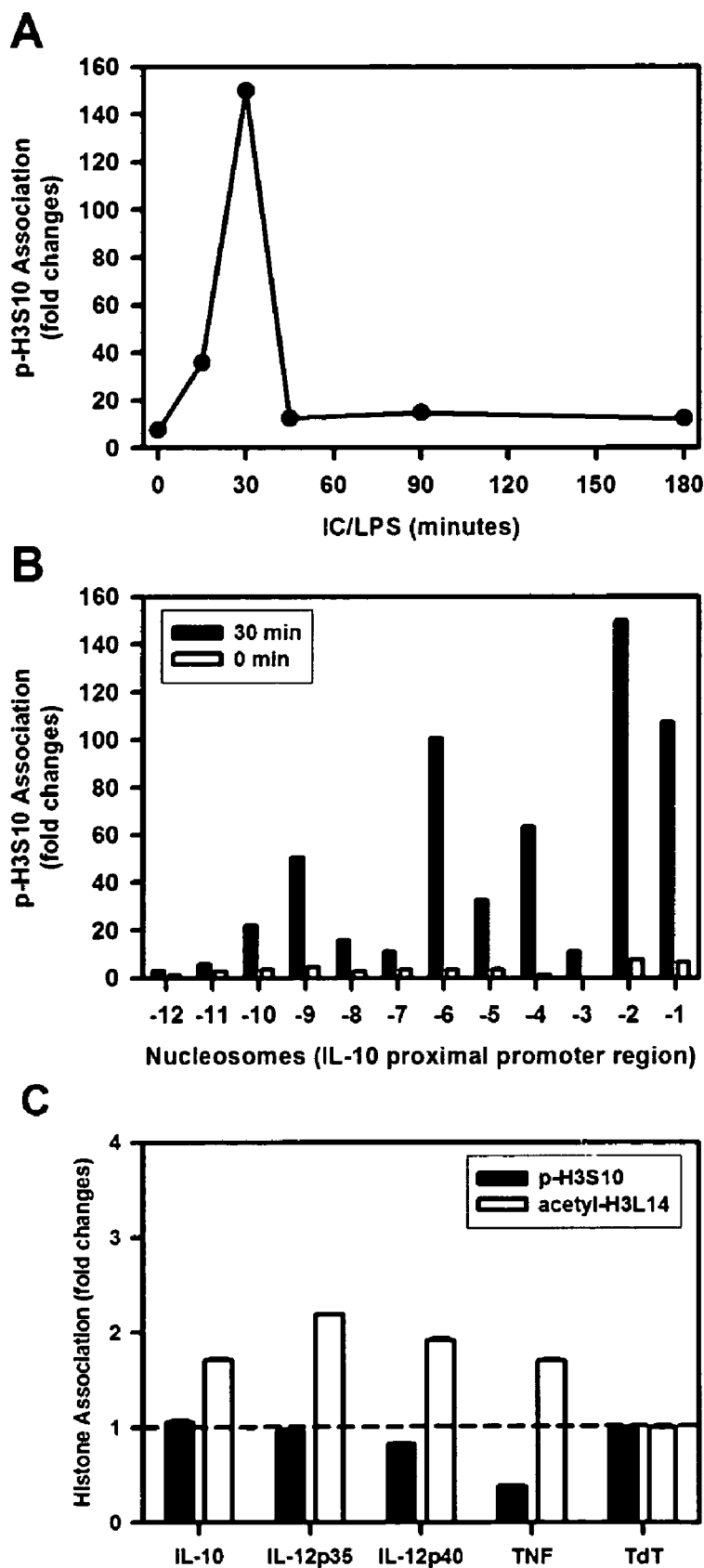
FIG. 16 are graphs showing histone H3 phosphorylation of Ser 10 in nucleosomes associated with the promoter region of IL-10. (A) BMMφ were stimulated with immune complexes plus 10 ng/mL LPS (IC/LPS) for 0, 15, 30, 45, 90, and 180 min. Cross-linked chromatin fragments were immunoprecipitated with anti-phosphorylated histone H3 Ser 10 antibody. The DNA was purified and examined for the presence of IL-10 promoter sequences corresponding to nucleosome −2 by quanitative RT-PCR (QRT-PCR). The data were normalized to inputs at each time point and plotted graphically as fold changes relative to the data at 0 min. (B) Immunoprecipitated DNA from the 30 min ChIP assay described in (A) was amplified with primers specific to each of the 12 nucleosomes by QRT-PCR. One representative experiment from three independent experiments is presented. (C) ChIP assay to amplify segments of the IL-10, IL-12 (p35 and 40), and TNF-α promoters following immunoprecipitations with antibody to phosphorylated (closed bars) or acetylated (open bars) histone H3. Levels were normalized to amplified TdT segment that was arbitrarily set as 1.

Macrophages were stimulated with LPS+IC and the phosphorylation of histone H3 at Ser 10 along the promoter region of the IL-10 gene was analyzed by ChIP. Initially we examined the second nucleosome from the transcription start site, because this is the location of the binding site to the transcription factor Sp1 (Brightbill, H. D., et al. 2000. J. Immunol. 164:1940). Phosphorylation of histone H3 at this site is rapid and peaks within 30 minutes of stimulation (FIG. 16A). This peak of histone phosphorylation is remarkably transient and is reduced to baseline levels by 60 minutes post-stimulation (FIG. 16A). We performed a similar analysis to quantify phosphorylation over the entire proximal 1600 bp of the IL-10 promoter. Although there was a substantial increase in histone phosphorylation throughout much of this region following stimulation, there were clear differences in the degree to which individual nucleosomes were modified. The highest degree of phosphorylation was observed at regions corresponding to the first two nucleosomes, but regions corresponding to nucleosomes −4 and −6 were also highly phosphorylated. These regions correspond to segments of the IL-10 promoter that are binding sites to the transcription factors implicated in IL-10 gene expression (Im, S. H., et al. 2004. J. Biol. Chem.). The distal-most segments analyzed, which correspond to nucleosomes −12 and −11, were not phosphorylayted to any substantial degree, nor were some of the intermediate nucleosomes eg. −3, −7. Thus, there appears to be a rapid and transient phosphorylation of nucleosomes across the IL-10 promoter in stimulated cells. These phosphorylation events do not appear to be random, but rather generally correspond to, or are adjacent to, segments of the promoter that bind to transcription factors.

In unstimulated macrophages there was little detectable phosphorylation at any of these locations (FIG. 16B, open bars). The negligible degree of histone H3 phosphorylation and acetylation in resting cells was similar for three different cytokines analyzed (IL-10, IL-12 and TNF-α) and comparable to the lymphocyte-specific TdT gene that is not expressed in macrophages (Zhou, L., et al. 2004. Mol. Cell Biol. 24:2385.) (FIG. 16C).

Acetylation of Histone H3 at Lys 14 on the IL-10 Promoter

Figure 17:
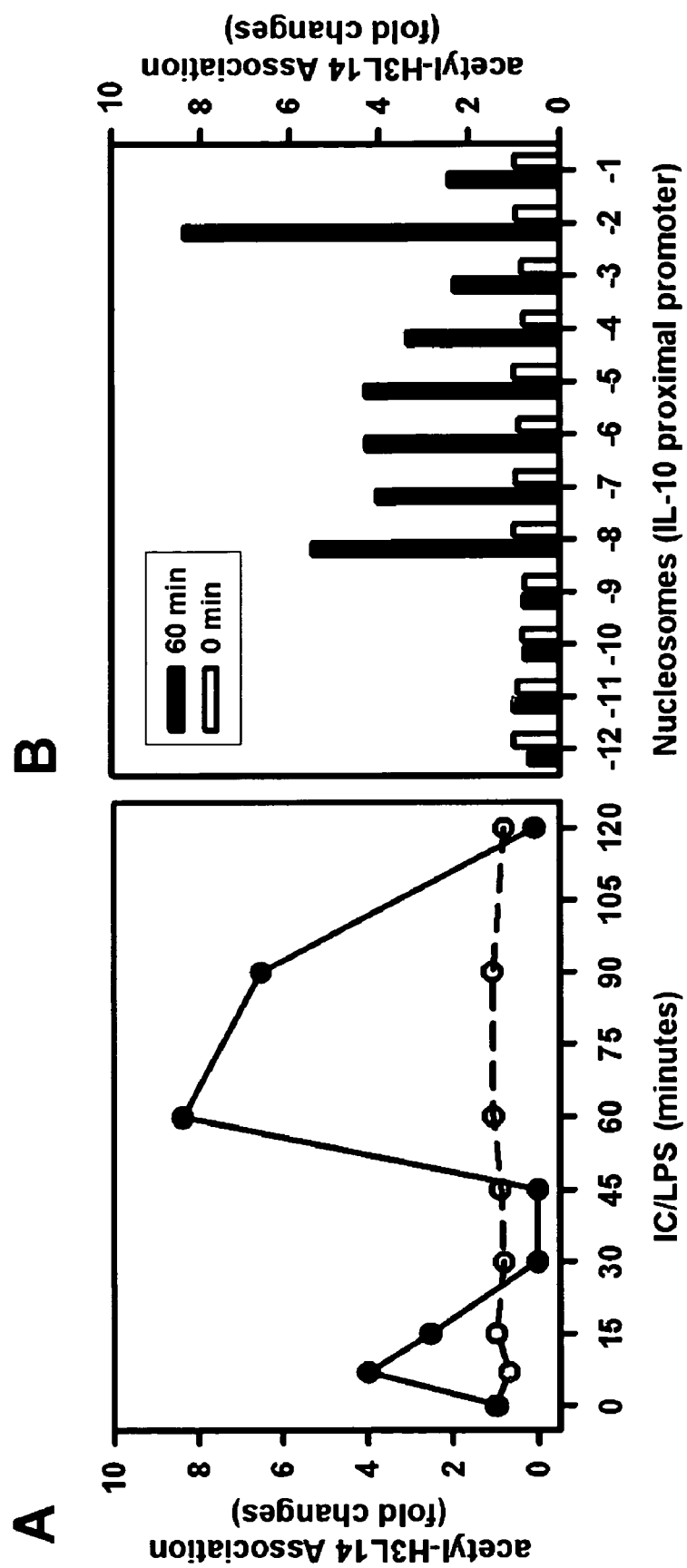
FIG. 17 are graphs showing histone H3 acetylation of Lys 14 on nucleosomes associated with the promoter region of IL-10. (A) BMMφ were stimulated with IC+LPS (10 ng/mL) for 0, 10, 15, 30, 45, 60, 90, and 120 min. Cross-linked chromatin fragments were immunoprecipitated with an antibody to acetylated histone H3 at Lys 14. The DNA was purified and analyzed for the presence of IL-10 promoter sequences corresponding to nucleosomes −2 (closed circles) and −12 (open circles) by QRT-PCR. The data were normalized to inputs at each time point and plotted graphically as fold changes relative to the data at 0 min. (B) The recovered DNA from the 60 minute ChIP assay described in (A) was amplified with primers specific to each of the 12 nucleosomes by QRT-PCR. One representative from two independent experiments is presented.

The acetylation of histones is an important modification that has been implicated in controlling gene expression (Struhl, K. 2005. Mol. Cell 17:752). We examined the acetylation of histone H3 at Lys14 across the IL-10 promoter region over time. Although transient low levels of lysine acetylation of histone H3 at nucleosome 2 were detectable within the first 15 minutes of stimulation, the main peak of acetylation was not detected until 60 minutes after stimulation (FIG. 17A). By 120 minutes, this peak of acetylation had returned to baseline. The pattern and extent of acetylation was distinct from that observed with phosphorylation (FIG. 17B). The extent of acetylation at nucleosome 2 was modest relative to the extent of phosphorylation, and there were low levels of acetylation spanning a broad region corresponding to nucleosomes −3 to −8. There was no detectable acetylation at the distal regions of this promoter. Importantly, the peak of acetylation did not occur until 60 minutes after stimulation, a time by which the phosphorylation of histones was returning to baseline.

Kinetics of Sp1 Recruitment to the IL-10 Promoter

Figure 18:
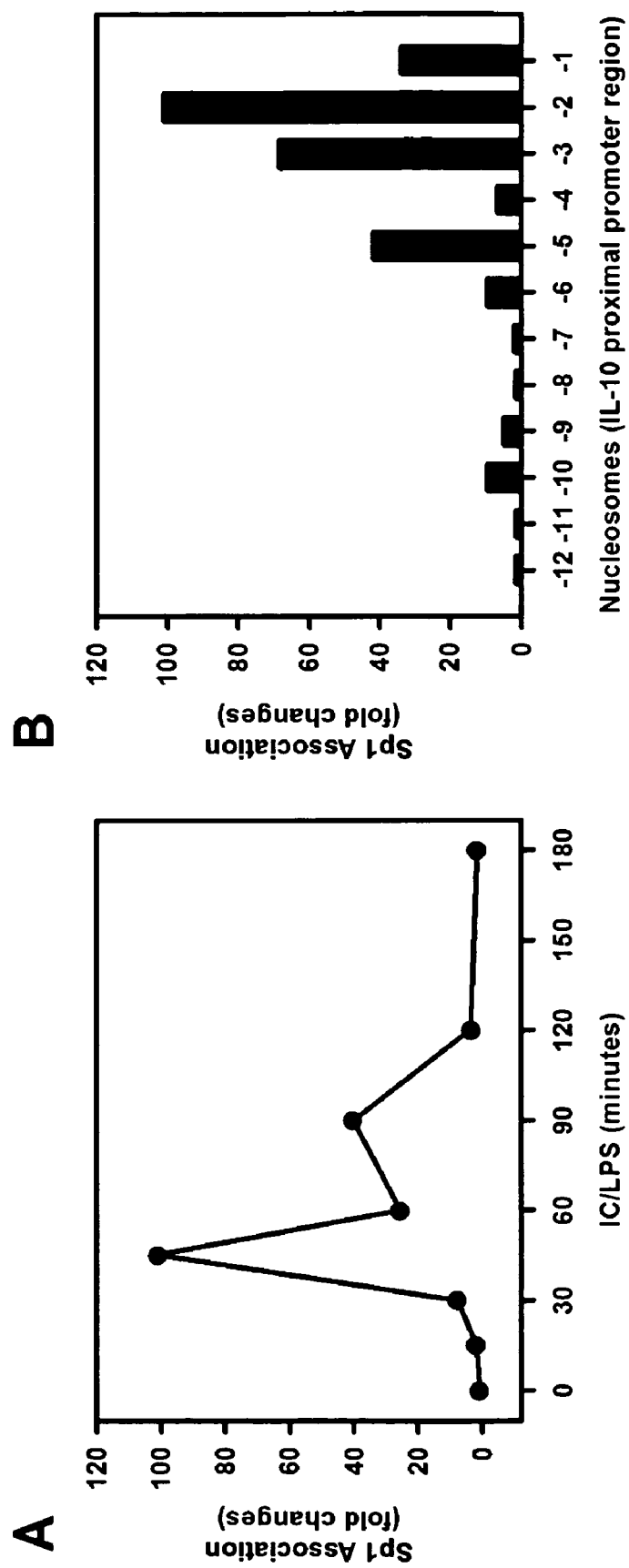
FIG. 18 are graphs showing recruitment of the Sp1 transcription factor to the IL-10 promoter. (A) BMMφ were stimulated with IC plus LPS (10 ng/mL) for 0, 15, 30, 45, 60, 90, 120, and 180 min. Cross-linked chromatin fragments were immunoprecipitated with anti-Sp1 antibody. The DNA was isolated and examined for the presence of IL-10 promoter sequences corresponding to nucleosome −2 by QRT-PCR. The data were normalized to inputs at each time point and plotted graphically as fold changes relative to the data at 0 min. (B) The recovered DNA from the 45 minute ChIP assay described in (A) was amplified with primers specific to each of the 12 nucleosomes by QRT-PCR. One representative from two independent experiments is presented.

Because Sp1 has been shown to play an important role in the regulation of IL-10 gene expression (Brightbill, H. D., et al. 2000. J. Immunol. 164:1940) and because this area of the promoter was rapidly phosphorylated, we assessed the kinetics of Sp1 recruitment to the IL-10 promoter. Macrophages were stimulated with LPS+IC, and then Sp1 was immunoprecipitated for ChIP and analyzed over time. Sp1 could not be detected on the promoter for the first 30 minutes post stimulation. After this lag, however, Sp1 was rapidly recruited to the promoter, reaching a peak at 45 min post-treatment and gradually declining thereafter (FIG. 18A). The recruitment of Sp1 was highest in the area surrounding the Sp1 binding site (5'-GGAGGAGGAGCC-3') (SEQ ID NO: 58) in the nucleosome −2 (−196 bp to −76), however, there was also a significant degree of Sp1 recruitment to the area corresponding to nucleosome −5 (−594 bp to −417 bp) that contained two potential Sp1 binding sites (5'-CTGCCCCACAGCAC-3' (SEQ ID NO: 59); 5'-AAAATCAGCCCTCT-3') (SEQ ID NO: 60) (FIG. 18B). Importantly, the kinetics of Sp1 recruitment to the area corresponding to nucleosome 2 followed temporally the phosphorylation of histone H3 at this site (see FIG. 16A).

Kinetic Analysis of IL-10 Gene Transcription.

Figure 19:
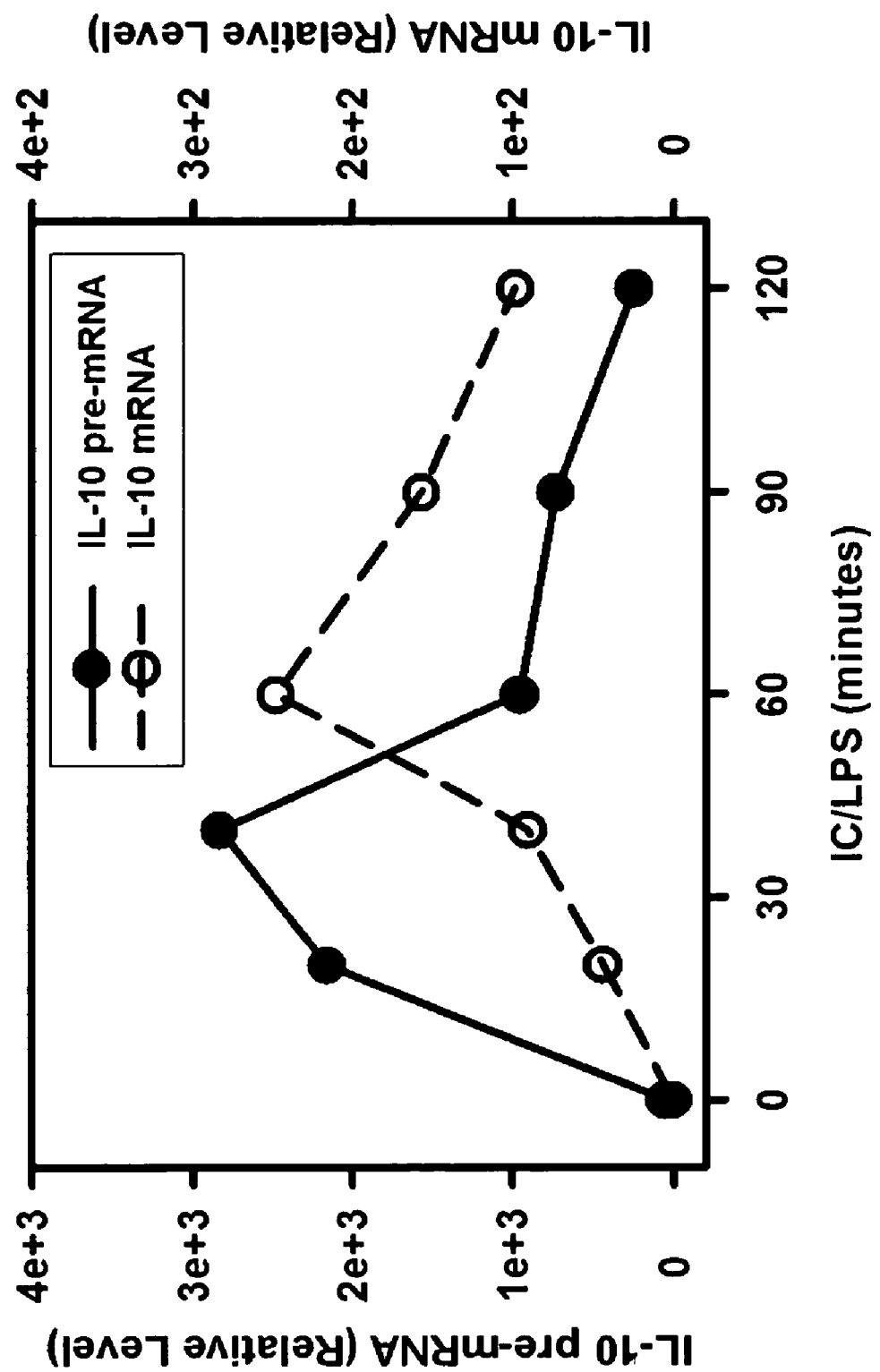
FIG. 19 is a graph showing IL-10 Gene Transcription and mRNA Accumulation in macrophages. BMMφ were stimulated with IC plus LPS (10 ng/mL) for 0, 20, 40, 60, and 120 min. RNA isolated from the cytoplasm and nucleus was purified and treated with RNase-free DNase I. Cytoplasmic and nuclear RNA were reverse transcribed to cDNA using oligo-dT$_{20}$ primer and random hexamers, respectively. The generated cDNA was then subjected to QRT-PCR analysis. The IL-10 RNA levels were presented as arbitrary units that were derived from average normalization values of each sample at each time point by corresponding GAPDH. The IL-10 mRNA level at zero time point was arbitrarily set as 1. Results presented are one representative from two independent experiments run in triplicate.

We next compared the kinetics of histone modifications with the induction of IL-10 transcription. To do this we measured the levels of premature nuclear mRNA. This premature mRNA contains introns and therefore the amplification of mRNA using an intron-specific primer can be used as an indicator of gene transcription (Goriely, S., et al. 2004. *J. Exp. Med.* 199:1011). IL-10 pre-mRNA accumulation in macrophages treated with LPS+IC was rapid and dynamic. It was detectible by as early as 15 min and it peaked at 45 min post-stimulation. By 120 minutes after stimulation pre-mRNA levels had receded to background levels. As expected, mature IL-10 mRNA accumulation took slightly longer to be produced and it persisted longer (FIG. 19).

Figure 20:
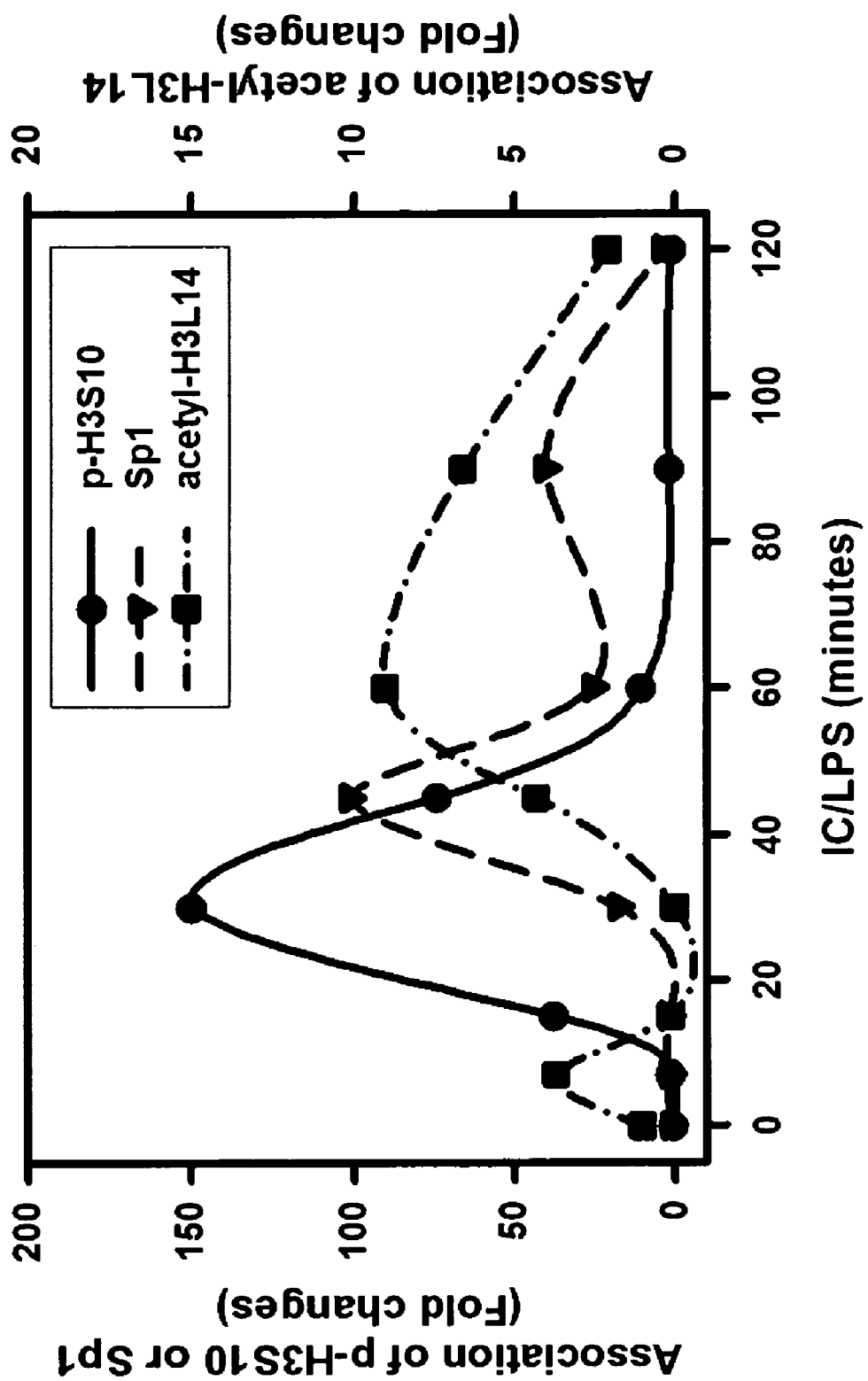
FIG. 20 is a graph showing the kinetics of histone H3 phosphorylation, Sp1 recruitment, and histone H3 acetylation on nucleosome −2. BMMφ were stimulated with IC plus LPS (10 ng/mL) for 0, 10, 15, 30, 45, 60, 90, and 120 min. Cross-linked chromatin fragments were immunoprecipitated with antibody to phosphorylated histone H3 at Ser 10, Sp1 antibody, and antibody to acetylated histone H3 at Lys 14, respectively. The DNA was purified and analyzed for the presence of IL-10 promoter sequences corresponding to nucleosome −2 by QRT-PCR. The data were normalized to inputs at each time point and plotted graphically as fold changes relative to the data at 0 min.

There was a close temporal association between the production of IL-10 pre-mRNA, and both the phosphorylation of histones, and the binding of Sp1 to the IL-10 promoter (FIG. 20). Phosphorylation at the Sp1 site peaked at 30 minutes. The binding of Sp1 and the production of IL-10 pre-mRNA transcripts peaked at 45 minutes (FIG. 20). The acetylation of histones, at this or other sites in the promoter, did not peak until 60 minutes, a time by which transcription was declining and Sp1 was no longer associated with the promoter. This later observation suggested that the acetylation of histones was not playing a primary role in IL-10 transcription.

Figure 21:
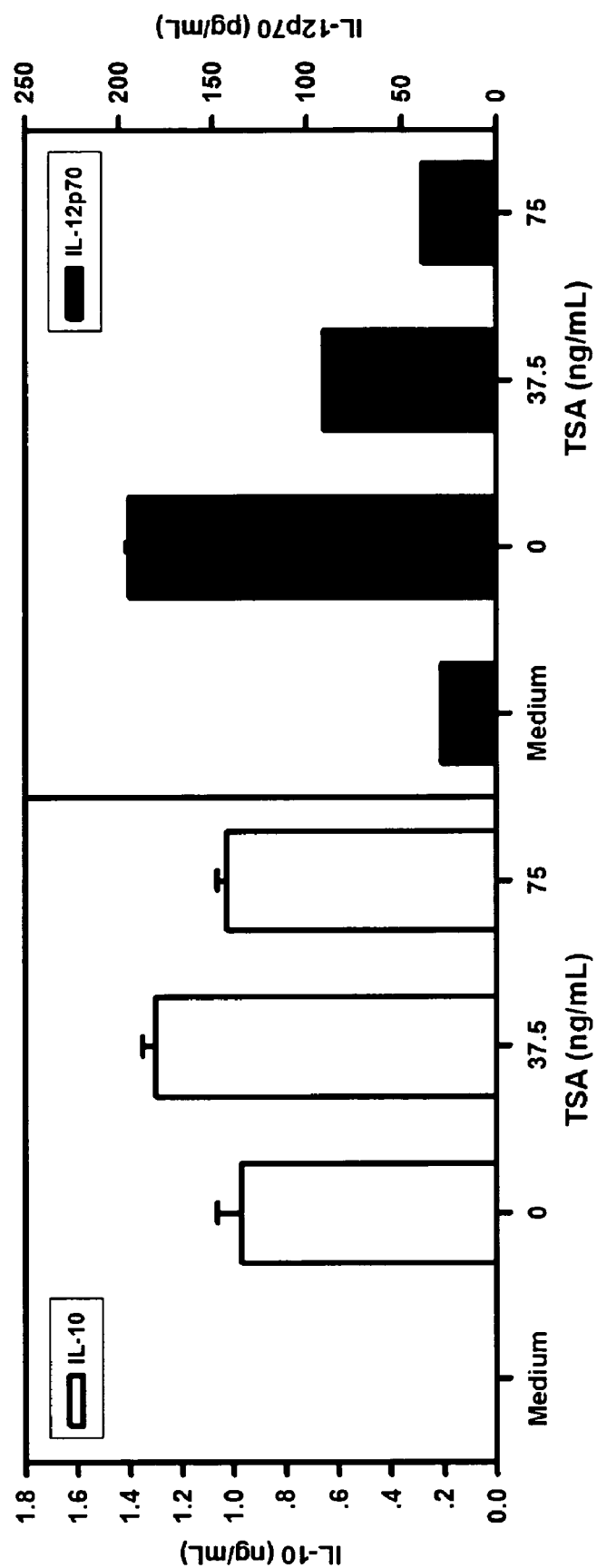
FIG. 21 is a graph showing cytokine production following histone deacetylation. TSA was added to BMMφ for 1 hr and the cells were then washed with warmed medium before stimulation with 10 ng/ml LPS+IC. After LPS+IC stimulation for 6 hrs, the supernatants were collected and IL-10 and IL-12 were measured by ELISA. Results shown are one representative from two independent experiments conducted in triplicate (mean±SD).

To further examine histone acetylation, macrophages were treated with increasing doses of the HDAC inhibitor, TSA, prior to stimulation. IL-10 levels were measured 6 hrs later. The inhibition of deacetylation failed to influence IL-10 production when added to cells at levels that were sufficient to substantially inhibit IL-12 (FIG. 21). This observation is consistent with the hypothesis that an increase in histone H3 acetylation was not a pre-requisite for IL-10 gene transcription following stimulation by LPS+IC.

The Role of ERK in Chromatin Phosphorylation

Figure 22:
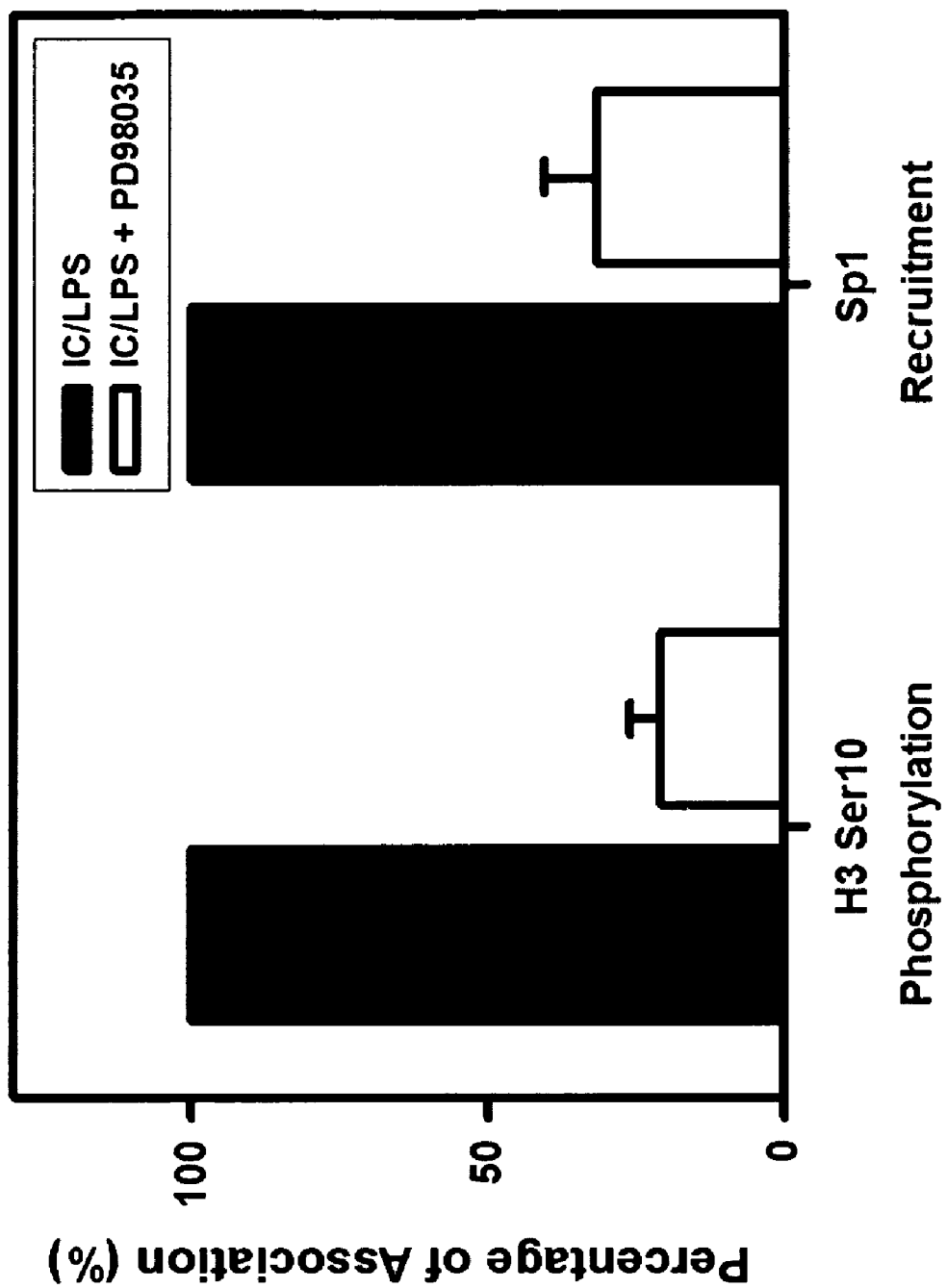
FIG. 22 is a graph showing Inhibition of histone modifications by blocking ERK. BMMφ were pre-treated with PD98059 (15 µM) (solid bars) or drug vehicle (open bars) for 1 hour and then stimulated with IC plus LPS (10 ng/mL). Cross-linked chromatin fragments were immunoprecipitated with antibody to phosphorylated histone H3 at Ser 10 or antibody to Sp1. The DNA was purified and analyzed for the presence of IL-10 promoter sequences corresponding to nucleosome −2 by QRT-PCR. The data were plotted graphically as the percentage change relative to drug vehicle (IC/LPS) at 30 min post-stimulation for histone H3 phosphorylation, and at 45 min post-stimulation for Sp1 recruitment. One representative from two independent experiments is presented.

We previously reported that maximal IL-10 production by macrophages depended on ERK activation (Lucas, M., X. Zhang, et al. 2005. *J. Immunol.* 175:469). In the present work we examined the levels of histone H3 phosphorylation and Sp1 recruitment to the IL-10 promoter following treatment of cells with PD98059, an inhibitor of ERK activation. Treatment of macrophages with PD98059 resulted in a substantial loss of histone H3 phosphorylation (FIG. 22). Sp1 recruitment was also dramatically reduced after treatment with PD98059 (FIG. 22). These data are consistent with the hypothesis that ERK activation leads to the phosphorylation of chromatin at the IL-10 promoter, allowing the recruitment of Sp1 to the promoter.

Figure 23:
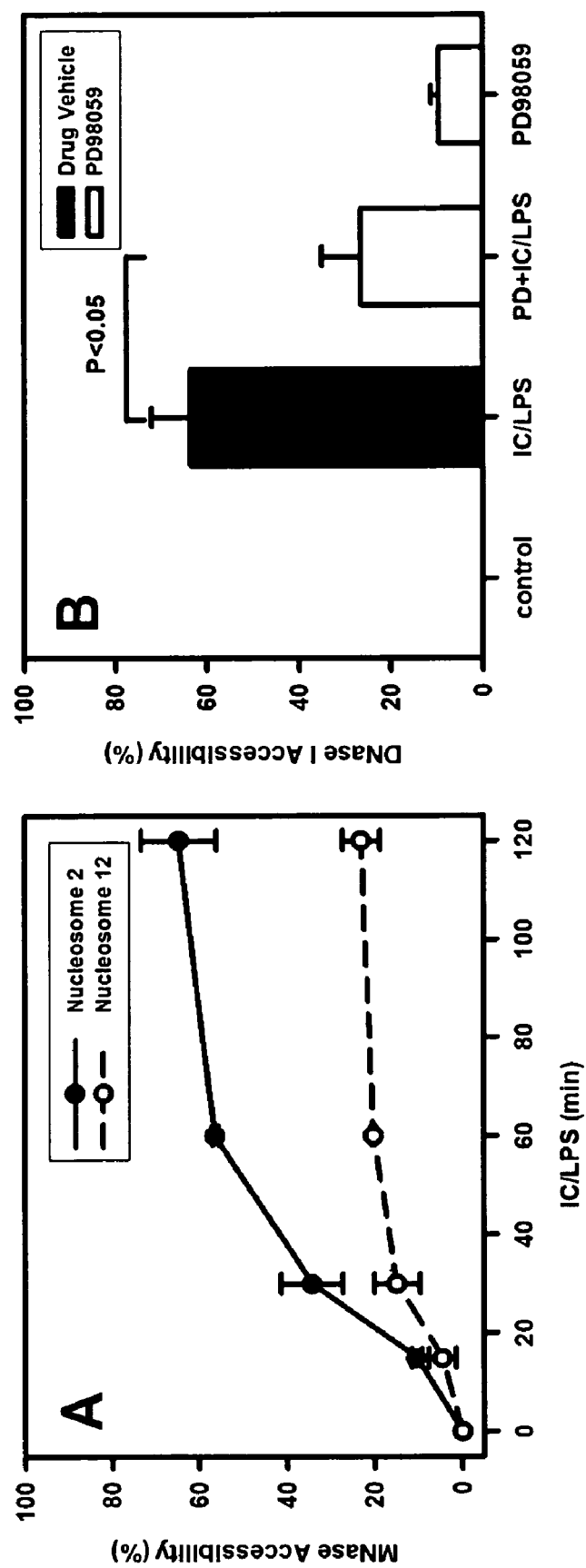
FIG. 23 are graphs showing enhanced chromatin accessibility following ERK activation. (A) BMMφ were stimulated with IC plus LPS (10 ng/mL) for 0, 15, 30, 60, and 120 min. Nuclei were isolated at each time point post-stimulation and treated with or without MNase. DNA was purified and analyzed for the presence of sequences corresponding to nucleosomes −2 and −12 by QRT-PCR. The data were graphically plotted as percentage of MNase accessibility relative to the samples of stimulation at zero time point. (B) BMMφ were pre-treated with PD98059 (15 µM) (open bars) or drug vehicle control (solid bars) for 1 hour and then stimulated with IC plus LPS (10 ng/mL) for 60 min. Nuclei were isolated from each group and treated with or without DNase I followed by extraction of genomic DNA. The presence of sequences corresponding to nucleosome −2 was examined by QRT-PCR. The data were expressed as percentage of DNase I accessibility relative to undigested genomic DNA sample and graphically plotted for each treated group. One representative from two independent experiments is presented. Each experiment was run in triplicate and shown as mean±SD.

The ERK-dependent binding of Sp1 to the IL-10 promoter suggested that histone phosphorylation might increase chromatin accessibility, possibly due to nucleosome disassembly or sliding of nucleosomes away from the promoter (Boeger, H., et al. 2004. *Mol. Cell* 14:667). To address this, we examined the sensitivity of DNA to cleavage by nucleases in the presence or absence of ERK inhibition. Chromatin sensitivity to MNase was measured at nucleosome 2 and compared to nucleosome 12 (FIG. 23A). In unstimulated cells (time 0) this region was relatively resistant to MNase cleavage. By 30 minutes post-stimulation there was a dramatic increase in MNase cleavage at nucleosome 2. Nucleosome 12 also exhibited a small increase in MNase sensitivity but it was significantly lower than nucleosome 2. Cleavage accessibility at nucleosome 2 peaked at 60 min post-stimulation and persisted for 120 min. Similar studies were performed using DNase (FIG. 23B). Similar to MNase treatment, nucleosome 2 was relatively resistant to cleavage in the absence of stimulation. The addition of LPS+IC resulted in a dramatic increase in cleavage. Inhibiting ERK by the addition of PD98059 reduced sensitivity to DNase by greater than half (FIG. 23B). These data indicate that histone H3 phosphorylation, initiated by the activation of ERK, was a critical event in inducing chromatin accessibility to the transcription factors that induce IL-10 production in macrophages.

Discussion

We previously demonstrated that activating macrophages in the presence of immune complexes leads to a specific hyperinduction of the cytokine, IL-10 (Sutterwala, F. S., et al. 1998. *J. Exp. Med.* 188:217). We recently made the observation that this hyperinduction requires activation of the MAPK pathway, leading to the phosphorylation of ERK (Lucas, M., X. Zhang, et al. 2005. *J. Immunol.* 175:469). In the present work, we explore the underlying molecular mechanisms by systemically examining the spatio-temporal changes of chromatin remodeling along the macrophage IL-10 promoter. We show that the phosphorylation of histones occurs mainly at the IL-10 promoter, and specifically at transcription factor binding sites in this promoter. We also show that the kinetics of histone phosphorylation closely follow the kinetics of both transcription factor binding and transcriptional activation. These results strongly suggest that phosphorylation is causally related to transcription.

This work suggests that the transcription of an anti-inflammatory cytokine, such as IL-10, is regulated by a more complex mechanism than the inflammatory cytokines, such as TNF-α. In addition to transcription factor activation a second level of regulation occurs at the level of chromatin. The speed and specificity of this second level of regulation are quite remarkable. The covalent modifications to histones occur within minutes of stimulation and they are reversed almost as quickly. The specificity of these modifications was also unexpected. Not only were these alterations specific to IL-10 and not to any of the other inflammatory cytokines examined, but segments of the IL-10 promoter located only 500 bases away from highly modified regions underwent no detectable phosphorylation changes throughout the observation period. As far as we are aware, this type of regulation has not been reported for any other cytokine to date.

There are aspects of this regulation that closely resemble the "nucleosome response" previously reported by Mahadevan and colleagues (Thomson, S., et al. 1999. *EMBO J.* 18:4779). In a series of studies, this group demonstrated that the nucleosome response is initiated by the activation of the MAPK cascade in response to cellular stressors. This leads directly to immediate early gene expression. This gene expression occurs in the absence of de novo protein synthesis (Clayton, A. L., and L. C. Mahadevan. 2003. *FEBS Lett.* 546:51), and in some cases the transcription factors are already associated with their respective DNA binding elements (Thomson, S., et al. 1999. *EMBO J.* 18:4779). We show that a similar cellular response occurs when macrophages encounter immune complexes. The histones are similarly phosphorylated in response to MAPK activation. However in the case of IL-10, this phosphorylation does not result in gene expression. Macrophages exposed to immune complexes alone produce no IL-10, despite the activation of ERK and the phosphorylation of histones. Rather, transcription of the IL-10 gene requires a second set of signals provided by TLR stimulation. This stimulation activates the necessary transcription factors, allowing them to bind to the phosphorylated chromatin which is now accessible to them. Thus, the induction of this anti-inflammatory cytokine is more complex than many of the inflammatory cytokines, whose synthesis mainly requires the recruitment of transcription factors and histone acetylation (Saccani, S., et al. 2002. p38, *Nat. Immunol.* 3:69; Avni, O., et al. 2002. *Nat. Immunol.* 3:643).

The now well-described concept of the "histone code" predicts that patterns of histone modifications at specific genes can affect gene expression (Cheung, P., et al. 2000. *Cell* 103:263; Wood, A., et al. 2005. *Biochem. Cell Biol.* 83:460). In the simplest terms, these modifications can influence the recruitment of transcription factors, polymerases, and co-activators to enhance or inhibit gene expression (Kornberg, R. D. 2005. *Trends Biochem. Sci.* 30:235). In dividing cells, these modifications can be quite complex, including mono, di, and trimethylation, ubiquitination, or even sumoylation (Mellor, J. 2005. *Mol. Cell* 19:147). These covalent modifications can "mark" chromatin for specific patterns of gene expression. In daughter cells the gene expression profile is preserved over many generations, despite the condensation of chromosomes during mitosis. The marking of chromatin for cytokine gene expression has recently been reported in T cells. In the case of IL-4, Th2-specific enhancement of histone acetylation and DNA demethylation in the control locus allows Th2 cells to continue to produce IL-4 following daughter cell division (Lee, D. U., et al. 2002. *Immunity* 16:649; Fields, P. E., et al. 2004. *Immunity* 21:865). A similar picture is emerging with regard to IL-10 production in T cells, where chromatin accessibility may predict stable IL-10 gene expression (Im, S. H., et al. 2004. *J. Biol. Chem.*). Unlike T cells, macrophages are end-stage cells that do not divide and therefore need no long term marking of the IL-10 gene. In fact, the sustained production of IL-10 in Th2 cells and their progeny (O'Garra, A., and P. Vieira. 2004. *Nat. Med.* 10:801) is quite distinct from the transient expression of IL-10 observed in macrophages. Thus, it was likely that different mechanisms would exist for regulating IL-10 gene expressions in macrophages relative to T cells. In T cells chromatin modifications accumulate slowly over generations and they are maintained in daughter cells. In macrophages histone phosphorylation was dynamically regulated across the IL-10 proximal promoter. It peaks within 30 minutes of stimulation and then rapidly disappears. The time of histone H3 phosphorylation corresponds closely with the kinetics of the production of IL-10 pre-mRNA.

Similar to previous studies with other genes and other systems (Nowak, S. J., and V. G. Corces. 2004. *Trends Genet.* 20:214; He, Z., et al. 2005. *J. Biol. Chem.* 280:2446), the acetylation of histone H3 at the IL-10 promoter follows histone H3 phosphorylation. Unlike many of these other systems, however, this modification does not appear to coincide with transcriptional activation. First, transcription factors bind to the promoter before acetylation occurs, and are in fact released from the promoter by the time that acetylation peaks. Second, the production of IL-10 pre-mRNA transcripts climaxes and declines before histone acetylation crests. Finally, treating macrophages with HDAC inhibitors does not affect IL-10 levels. Thus, whereas histone H3 phosphorylation temporally correlates with IL-10 gene expression, acetylation does not.

Our results predict that the phosphorylation of histones is tightly associated with transcriptional activation of the IL-10 gene. In other cellular systems, the phosphorylation of histones is not always associated with gene activation. In fact, histone H3 is highly phosphorylated on serine 10 on condensed chromatin during mitosis (Cheung, P., et al. 2000. *Cell* 103:263). Unlike the phosphorylation events associated with mitosis, however, the immune complex-induced phosphorylation that we observe is specific to individual regions of the IL-10 promoter rather than uniform, and it is far more transient. Studies are underway to identify the kinase(s) responsible for histone phosphorylation, and the phosphatase(s) mediating the rapid dephoshosphrylation of histones following activation. We predict that mechanisms to prolong histone phosphorylation may be exploited to manipulate macrophage IL-10 production.

In summary, we provide a detailed analysis of the modifications of the nucleosomes associated with the promoter region of IL-10 gene. We show that the evanescent, ERK-dependent, phosphorylation of histone H3 at Ser 10 is essential for IL10 superinduction. These studies provide a molecular understanding of IL-10 gene regulation in macrophages, which may lead to novel ways to manipulate IL-10 levels. Since the production of high levels of IL-10 can either result in a beneficial anti-inflammatory response, or a pathological immunosuppressive response, new ways to manipulate the production of this cytokine can be used to enhance or inhibit immune responses, as necessary.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed:

1. A method of upregulating IL-10 production above that in resting cells in a macrophage-like cell in response to an inflammatory stimulus comprising contacting said cell with a composition comprising an extracellular-signal-regulated kinase (ERK) activating agent in combination with a phosphatase inhibitor wherein the ERK activating agent is selected from colony stimulating factor 1 (CSF-1) or immune complexes (IC) wherein the macrophage-like cell is selected from the group consisting of bone marrow derived macrophages, leukocytes and dendritic cells and wherein the immune complexes are IgG immune complexes.

2. The method of claim 1 wherein the phosphatase inhibitor is selected from the group consisting of okadaic acid, sodium orthovanadate, NaVa4, cnataridin, 1 naphthyphosphate sodium salt, $Na_3VO_4$, NaF, b-glycerphosphate, rapamycin and tacrolimus.

3. The method of claim 1 wherein the inflammatory stimulus is selected from the group consisting of CD40-L, bacteria or bacterial components.

4. The method of claim 3 wherein the bacterial components are bacterial cell walls such as lipopolysaccharide (LPS) or lipotechoic acid.

5. The method of claim 1 wherein upregulation of IL-10 production is sustained for at least 30 minutes.

6. The method of claim 1 wherein the immune complexes are E-IgG.

7. The method of claim 1 wherein the immune complexes are soluble.

8. The method of claim 7 wherein the soluble immune complexes are Ig-OVA.

* * * * *

SEQUENCE LISTING

<160> NUMBER OF SEQ ID NOS: 61

<210> SEQ ID NO 1
<211> LENGTH: 15
<212> TYPE: DNA
<213> ORGANISM: Artificial Sequence
<220> FEATURE:
<223> OTHER INFORMATION: Synthetic

```
<400> SEQUENCE: 1
ccacaaagcc ttgca                                                    15

<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2
agtaagagca ggcagcatag ca                                            22

<210> SEQ ID NO 3
<211> LENGTH: 29
<212> TYPE: DNA
<213> ORGANISM: Artificial Sequence
<220> FEATURE:
<223> OTHER INFORMATION: Synthetic

<400> SEQUENCE: 3
aactggcact tcacgatcct gcctgtctc                                     29

<210> SEQ ID NO 4
<211> LENGTH: 29
<212> TYPE: DNA
<213> ORGANISM: Artificial Sequence
<220> FEATURE:
<223> OTHER INFORMATION: Synthetic

<400> SEQUENCE: 4
aacaggatcg tgaagtgcca gcctgtctc                                     29

<210> SEQ ID NO 5
<211> LENGTH: 28
<212> TYPE: DNA
<213> ORGANISM: Artificial Sequence
<220> FEATURE:
<223> OTHER INFORMATION: Synthetic

<400> SEQUENCE: 5
acttgatggc cactctggtc cctgtctc                                      28

<210> SEQ ID NO 6
<211> LENGTH: 29
<212> TYPE: DNA
<213> ORGANISM: Artificial Sequence
<220> FEATURE:
<223> OTHER INFORMATION: Synthetic

<400> SEQUENCE: 6
aagaccagag tggccatcaa gcctgtctc                                     29

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
caggatcgtg aagtgccaga a                                             21
```

<210> SEQ ID NO 8
<211> LENGTH: 19
<212> TYPE: DNA
<213> ORGANISM: Artificial Sequence
<220> FEATURE:
<223> OTHER INFORMATION: Synthetic

<400> SEQUENCE: 8
gccctcggag gatctggta                                                    19

<210> SEQ ID NO 9
<211> LENGTH: 24
<212> TYPE: DNA
<213> ORGANISM: Artificial Sequence
<220> FEATURE:
<223> OTHER INFORMATION: Synthetic

<400> SEQUENCE: 9
tgttataggc atccgagaca tcct                                              24

<210> SEQ ID NO 10
<211> LENGTH: 25
<212> TYPE: DNA
<213> ORGANISM: Artificial Sequence
<220> FEATURE:
<223> OTHER INFORMATION: Synthetic

<400> SEQUENCE: 10
ccatgaggtc ctgaacaatg taaac                                             25

<210> SEQ ID NO 11
<211> LENGTH: 25
<212> TYPE: DNA
<213> ORGANISM: Artificial Sequence
<220> FEATURE:
<223> OTHER INFORMATION: Synthetic

<400> SEQUENCE: 11
cagctgtctg cctcaggaaa tacaa                                             25

<210> SEQ ID NO 12
<211> LENGTH: 25
<212> TYPE: DNA
<213> ORGANISM: Artificial Sequence
<220> FEATURE:
<223> OTHER INFORMATION: Synthetic

<400> SEQUENCE: 12
tattcaggct cctcctccct cttct                                             25

<210> SEQ ID NO 13
<211> LENGTH: 22
<212> TYPE: DNA
<213> ORGANISM: Artificial Sequence
<220> FEATURE:
<223> OTHER INFORMATION: Synthetic

<400> SEQUENCE: 13
tcatgctggg atctgagctt ct                                                22

<210> SEQ ID NO 14
<211> LENGTH: 23
<212> TYPE: DNA
<213> ORGANISM: Artificial Sequence
<220> FEATURE:
<223> OTHER INFORMATION: Synthetic

```
<400> SEQUENCE: 14
cggaagtcac cttagcactc agt                                          23

<210> SEQ ID NO 15
<211> LENGTH: 21
<212> TYPE: DNA
<213> ORGANISM: Artificial Sequence
<220> FEATURE:
<223> OTHER INFORMATION: Synthetic

<400> SEQUENCE: 15
caaatctggg aggcaggaaa c                                            21

<210> SEQ ID NO 16
<211> LENGTH: 28
<212> TYPE: DNA
<213> ORGANISM: Artificial Sequence
<220> FEATURE:
<223> OTHER INFORMATION: Synthetic

<400> SEQUENCE: 16
caaagcaaac ctttctatca aatacaca                                     28

<210> SEQ ID NO 17
<211> LENGTH: 22
<212> TYPE: DNA
<213> ORGANISM: Artificial Sequence
<220> FEATURE:
<223> OTHER INFORMATION: Synthetic

<400> SEQUENCE: 17
cagtcaggag agagggcagt ga                                           22

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
tttccaacag cagaagcaac                                              20

<210> SEQ ID NO 19
<211> LENGTH: 21
<212> TYPE: DNA
<213> ORGANISM: Artificial Sequence
<220> FEATURE:
<223> OTHER INFORMATION: Synthetic

<400> SEQUENCE: 19
cattccagta agtcacaccc a                                            21

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
tctcacccag ggaattcaaa                                              20
```

```
<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
tgttcctacc cccaatgtgt                                                   20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
tcccaagtca ctgtcacacc                                                   20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
aaggaccagc tggacaacat                                                   20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
tctcacccag ggaattcaaa                                                   20

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
tgttcctacc cccaatgtgt                                                   20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
ggtcctcagt gtagcccaag                                                   20

<210> SEQ ID NO 27
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 27
tagaagaggg aggaggagcc                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
tgtggctttg gtagtgcaag                                              20

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
gcagaagttc attccgacca                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
ggctcctcct ccctcttcta                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
attatgacct gggagtgcgt                                              20

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
tggtcggaat gaacttctgc                                              20

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
aatatcggac gttcaaccca                                              20
```

```
<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
acgcactccc aggtcataat                                               20

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
ctctcctctg accaactgcc                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
tgggttgaac gtccgatatt                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
attgtaaaac agggccatgg                                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic

<400> SEQUENCE: 38
ggcagttggt cagaggagag                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
gttcttccca cccaaactga                                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 40
ccatggccct gttttacaat                                            20

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
aacattccct ggtcaacagg                                            20

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
tcagtttggg tgggaagaac                                            20

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
ggtgtggtaa ccctctccaa                                            20

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
cctgttgacc agggaatgtt                                            20

<210> SEQ ID NO 45
<211> LENGTH: 20
<212> TYPE: DNA
<213> ORGANISM: Artificial Sequence
<220> FEATURE:
<223> OTHER INFORMATION: Synthetic

<400> SEQUENCE: 45
aactcagcct ggaactgacc                                            20

<210> SEQ ID NO 46
<211> LENGTH: 20
<212> TYPE: DNA
<213> ORGANISM: Artificial Sequence
<220> FEATURE:
<223> OTHER INFORMATION: Synthetic

<400> SEQUENCE: 46
ttggagaggg ttaccacacc                                            20
```

```
<210> SEQ ID NO 47
<211> LENGTH: 20
<212> TYPE: DNA
<213> ORGANISM: Artificial Sequence
<220> FEATURE:
<223> OTHER INFORMATION: Synthetic

<400> SEQUENCE: 47
gttgcttctg ctgttggaaa                                               20

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
ggtcagttcc aggctgagtt                                               20

<210> SEQ ID NO 49
<211> LENGTH: 22
<212> TYPE: DNA
<213> ORGANISM: Artificial Sequence
<220> FEATURE:
<223> OTHER INFORMATION: Synthetic

<400> SEQUENCE: 49
cagtcaggag agagggcagt ga                                            22

<210> SEQ ID NO 50
<211> LENGTH: 20
<212> TYPE: DNA
<213> ORGANISM: Artificial Sequence
<220> FEATURE:
<223> OTHER INFORMATION: Synthetic

<400> SEQUENCE: 50
tttccaacag cagaagcaac                                               20

<210> SEQ ID NO 51
<211> LENGTH: 23
<212> TYPE: DNA
<213> ORGANISM: Artificial Sequence
<220> FEATURE:
<223> OTHER INFORMATION: Synthetic

<400> SEQUENCE: 51
ccacatgaga tcatggtttt ctc                                           23

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
ctggctagtc ccttgctgtc                                               20

<210> SEQ ID NO 53
<211> LENGTH: 23
<212> TYPE: DNA
<213> ORGANISM: Artificial Sequence
<220> FEATURE:
<223> OTHER INFORMATION: Synthetic
```

```
<400> SEQUENCE: 53
tttcgacgtc tatattccct ctg                                    23

<210> SEQ ID NO 54
<211> LENGTH: 21
<212> TYPE: DNA
<213> ORGANISM: Artificial Sequence
<220> FEATURE:
<223> OTHER INFORMATION: Synthetic

<400> SEQUENCE: 54
cgacgcactt gtccttgaga t                                      21

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
actgagagga gctgctggat                                        20

<210> SEQ ID NO 56
<211> LENGTH: 22
<212> TYPE: DNA
<213> ORGANISM: Artificial Sequence
<220> FEATURE:
<223> OTHER INFORMATION: Synthetic

<400> SEQUENCE: 56
accaagactg acaacccacg tt                                     22

<210> SEQ ID NO 57
<211> LENGTH: 21
<212> TYPE: DNA
<213> ORGANISM: Artificial Sequence
<220> FEATURE:
<223> OTHER INFORMATION: Synthetic

<400> SEQUENCE: 57
gtggcagtca gaggcatctt t                                      21

<210> SEQ ID NO 58
<211> LENGTH: 12
<212> TYPE: DNA
<213> ORGANISM: Artificial Sequence
<220> FEATURE:
<223> OTHER INFORMATION: Synthetic

<400> SEQUENCE: 58
ggaggaggag cc                                                12

<210> SEQ ID NO 59
<211> LENGTH: 14
<212> TYPE: DNA
<213> ORGANISM: Artificial Sequence
<220> FEATURE:
<223> OTHER INFORMATION: Synthetic

<400> SEQUENCE: 59
ctgccccaca gcac                                              14
```

```
<210> SEQ ID NO 60
<211> LENGTH: 14
<212> TYPE: DNA
<213> ORGANISM: Artificial Sequence
<220> FEATURE:
<223> OTHER INFORMATION: Synthetic

<400> SEQUENCE: 60
aaaatcagcc ctct                                                        14

<210> SEQ ID NO 61
<211> LENGTH: 19
<212> TYPE: DNA
<213> ORGANISM: Artificial Sequence
<220> FEATURE:
<223> OTHER INFORMATION: synthetic

<400> SEQUENCE: 61
agctgcctgg tctgatgtg                                                   19
```